United States Patent [19]

Firestone

[11] 4,051,132
[45] Sept. 27, 1977

[54] PROCESS FOR EPIMERIZING BETA-LACTAM ANTIBIOTIC COMPOUNDS BY MEANS OF AN ACID QUENCH

[75] Inventor: Raymond A. Firestone, Fanwood, N.J.

[73] Assignee: Merck & Co., Inc., Rahway, N.J.

[21] Appl. No.: 644,250

[22] Filed: Dec. 24, 1975

Related U.S. Application Data

[63] Continuation of Ser. No. 436,014, Jan. 23, 1974, abandoned, which is a continuation-in-part of Ser. No. 350,543, April 16, 1973, abandoned, Ser. No. 303,906, Nov. 6, 1972, abandoned, Ser. No. 306,066, Nov. 13, 1972, abandoned, Ser. No. 314,484, Dec. 12, 1972, abandoned, Ser. No. 319,945, Dec. 29, 1972, abandoned, and Ser. No. 340,804, March 13, 1973, abandoned, said Ser. No. 350,543, is a continuation-in-part of Ser. No. 267,858, June 30, 1972, abandoned.

[51] Int. Cl.$^2$ ............................................. C07D 501/04

[52] U.S. Cl. ................................. 544/20; 260/244 R; 260/256.4 F; 260/295 F; 260/307 A; 544/19
[58] Field of Search ..................................... 260/243 C

[56] References Cited
U.S. PATENT DOCUMENTS 3,719,667    3/1973    Gutowski .......................... 260/239.1

Primary Examiner—Nicholas S. Rizzo
Assistant Examiner—James H. Turnipseed
Attorney, Agent, or Firm—Edmunde D. Riedl; Hesna J. Pfeiffer; Julian S. Levitt

[57] ABSTRACT

Total synthesis methods employ 7-amino (6-amino in the case of a penicillin derivative) group in the alpha configuration. The instant invention provides a general route for preparing the 7β-amino (or 6β-amino) compound, through the formation of an imino-containing intermediate, followed by hydrolysis to the desired epimer. Novel intermediate products are provided. The compounds having the desired beta epimer can be converted to acylamino-antibiotics.

22 Claims, No Drawings

PROCESS FOR EPIMERIZING BETA-LACTAM ANTIBIOTIC COMPOUNDS BY MEANS OF AN ACID QUENCH

RELATIONS TO OTHER APPLICATIONS

This application is a continuation of U.S. application Ser. No. 436,014 filed Jan. 23, 1974 now abandoned which was a continuation-in-part of U.S. application Ser. No. 350,543, filed Apr. 16, 1973, now abandoned, which was a continuation-in-part of U.S. application Ser. No. 267,858, filed June 30, 1972, now abandoned; this application is also a continuation-in-part of copending U.S. application Nos. 303,906, filed Nov. 6, 1972; 306,066, filed Nov. 13, 1972; 314,484, filed Dec. 12, 1972; 319,945, filed Dec. 29, 1972; and 340,804, filed Mar. 13, 1973; all now abandoned.

This invention relates to a process for changing the configuration of certain stereoisomeric cephem compounds.

The compounds prepared by the process of this invention are the following:

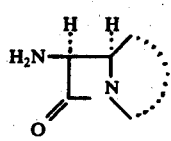

I wherein the symbol indicated as a dotted line represents the following groups:

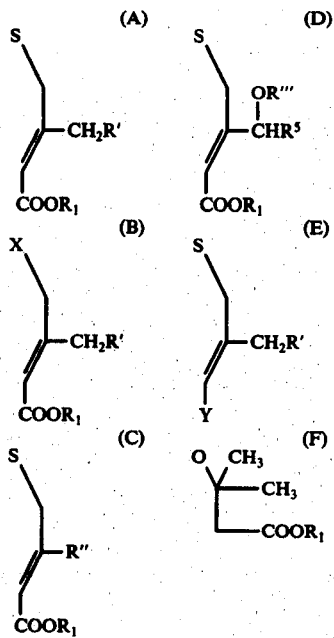

In all of these compounds, the substituent $R_1$ is an ester blocking or protecting group on the carboxy substituent, preferably one which can be removed easily without disruption of the β-lactam ring to yield the final active free acid. A number of protecting groups suitable for this purpose are now well recognized in the penicillin or cephalosporin art and can accordingly be used in the practice of this invention. Examples of suitable protecting ester groups that might be mentioned are those of alcohols, phenols, and the like. $R_1$ is preferably an alkyl or aralkyl group containing from 1 to about 20 carbon atoms. Thus, $R_1$ can be lower alkyl group such as methyl, ethyl or tertiary butyl, a substituted alkyl such as phthalimidomethyl, succinimidomethyl, phenacyl, substituted phenacyl such as p-bromophenacyl, a β-substituted ethyl group such as 2,2,2-trichloroethyl, 2-methylthioethyl, or 2-(p-methylphenyl)-ethyl, an alkoxyalkyl group such a methoxymethyl, an aryloxyalkyl such as p-methoxyphenoxymethyl, an aralkyloxyalkyl group such as benzyloxymethyl, benzyl or a substituted benzyl group such as p-nitrobenzyl, p-methoxybenzyl, 3,5-dinitrobenzyl, 2,4,6-trimethylbenzyl or 3,5-dichloro-4-hydroxy-benzyl, benzhydryl or a substituted benzhydryl group such as p-methoxybenzhydryl, and the like. $R_1$ can also be loweralkyl silyl, such as trimethylsilyl. Preferred blocking groups are methyl, tertiary butyl, phenacyl, p-bromophenacyl, 2,2,2-trichloroethyl, p-methoxybenzyl, benzhydryl, methoxymethyl, and p-methoxyphenoxymethyl.

In the compounds IA, IB and IE, the substituent R' is preferably hydrogen, halo, alkanoyloxy, carbamoyloxy, or heterocyclic thio. By the term "halo" is meant chloro, fluoro, bromo, or iodo. By the term "alkanoyloxy" is meant a lower alkanoic acid residue of 1–6 carbon atoms. By the termn "heterocyclic thio" is meant a 5-membered heterocyclic thio group having 1–4 hetero atoms, the latter being S, O, or N, otherwise having the structure

wherein Z is a 5-membered heterocyclic ring having oxa, aza, thia, dioxa, diaza, dithia, trioxa, triaza, trithia, tetra-aza, or mixed hetero atoms in the ring. Included within this definition are the heterocyclic rings listed above, as well as the following additional rings: 1H-tetrazole; 2H-tetrazole; 3H-1,2,3-oxathiazole; 1,4,2-oxathiazole; 5H-1,2,5-oxathiazole; 3H-1,2,4-dioxazole; 1,3,4-dioxazole; 1,2,4-dithiazole; 1,3,4-dithiazole; 1,2,3-oxadiazole; 1,2,4-oxadiazole; 1,2,5-oxadiazole; 1,3,4-oxadiazole; 1,2,3-thiadiazole; 1,2,4-thiadiazole; 1,2,5-thiadiazole; 1,3,4-thiadiazole; 1H-1,2,3-triazole; 1,2,5-oxadithiole; 1,3,2-dioxathiole; 1,2,3-trioxole; 1,2,4-trioxolane, 1,2,3-trithiole; 1,2,4-trithiolane, etc. The point of attachment can be in any suitable position of the ring.

Other suitable heterocyclic rings can be found in the literature, including the ACS monograph, *The Ring Index*, Ed. Capell et al., Second Edition (1957) and supplements (1959), (1962), (1965).

Representative of the hetero groups of interest that may be employed in the practice of the invention include furyl, thienyl, thiazolyl, thiadiazolyl, pyrrolyl, tetrazolyl, and the like or a substituted heterocyclic group having one or more alkyl, alkoxy, halo, cyano or carbo-alkoxy and the like. Two heterocyclic thio groups of particular interest are 5-methyl-1,3,4-thiadiazolyl-2-yl and 1-methyl-tetrazol-5-yl.

R' can also include a large number of substituents which have been provided in the 3-position of the cephalosporin or isosteric cephalosporin series, i.e., alkoxy, phenoxy, benzyloxy, alkoxyalkoxy, mono- or disubstituted carbamoyloxy, azido, cyano, a tertiary amine such as pyridinium, alkyl pyridinium, halo pyridinium, aminopyridinium, benzyl, substituted benzyl, phenethyl, substituted phenethyl, quaterary ammonium, thiocarbamoyloxy and substituted thiocarbamoyloxy, or benzoyloxy. When the term "substituted" is employed, it means having alkyl, halo, alkoxy, nitro or other groups on the basic chain. The terms alkyl or alkoxy are understood to indicate a chain having 1–6 carbon atoms.

In compound IB, the substituent X is a divalent radical, —O—, —CH$_2$— or —NQ— wherein Q is hydrogen, formyl, benzyl, or loweralkyl of 1–6 carbon atoms such as methyl, ethyl, propyl, butyl, pentyl or hexyl.

In compound IC, the substituent R″ is phenyl, a heterocyclic group. The heterocyclic group is preferably a 5- or 6-membered ring containing one, two, three or four sulfur, nitrogen, oxygen atoms such as furyl, thienyl, thiazolyl, thiadiazolyl, pyridyl, pyrazolyl, tetrazolyl, and the like. The substituents on the phenyl or heterocyclic group can be lower alkyl (C$_1$-C$_6$), lower alkoxy (C$_1$-C$_6$), halo, cyano, carboloweralkoxy, and the like.

In compound ID, R‴ is loweralkanoyl having 2–6 carbon atoms; and R$^5$ is a C$_1$-C$_3$ straight or branched chain alkyl group.

In compound IE, Y is a radical of the formula: PO(OH)$_2$; PO(OH) (OR$^4$); or SO$_2$(OH); or —SO$_2$NH$_2$, in which R$^4$ is loweralkyl of 1–6 carbon atoms, preferably methyl.

All of the above compounds are prepared by a total synthesis method developed in the assignee's laboratories, although the synthetic process does not form a part of this invention. The inventive process of this application is concerned exclusively with the epimerization step, that is, of the process of preparing compounds of formula I from their epimeric configuration, as in the following:

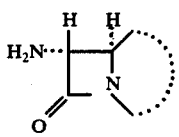

II wherein the dotted line represents the same groups, supra. It is understood that compounds of formulas IIA, IIB, IIC, IIE, and IIF are included within the general formula II. Since the identity of these groups indicated by the dotted line is not effected by, nor participates in, the epimerization reaction, the process is applicable to all compounds within formula II. It will be apparent to all skilled in the art that other beta-lactam compounds can also be employed in this epimerization process, including compounds made by other totally or partially synthetic methods. In addition, the instant epimerization process can be employed on mixtures of epimers if these are produced by synthetic methods; it is not necessary for the starting material to be free of its epimer for the process to be operable.

The compounds prepared by this process, containing the 7β- or 6β-amino group are used, following acylation, as new and useful antibiotics.

The acylated products, for instance, are effective against gram-positive and gram-negative bacteria. This activity includes effectiveness against many bacteria, including in vivo on *Escherichia coli*, *Proteus vulgaris*, *Salmonella schottmuelleri*, *Klebsiella pneumoniae* Ad, and *Klebsiella pneumoniae* B. Specific bacterial activity is dependent upon the exact structure of the final product; not all compounds are active against all organisms.

The final active antibiotic agents can be used to combat bacterial infections in animals or humans. They can be employed in dosages and administrative forms similar to that employed for commercially available cephalosporins and penicillins. Exact dose levels and modes of administration can be readily determined by one skilled in the art. Generally, between 0.1–500 mg./kg. body weight can be employed to give effective antibacterial control.

The final products can also be used in industrial applications where an antibacterial agent is useful in inhibiting undesirable bacterial growth. Salts of these products are particularly useful in paper mill white water applications, or in paints, especially polyvinyl acetate latex paint.

The nomenclature used in this application is further defined as follows:

The compound,

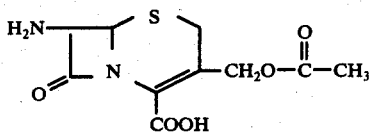

is called 7-aminocephalosporinic acid. The side chain at 3 is inherently contained in the name. By comparison, the skeleton

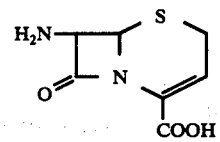

is called 7-aminodecephalosporanic acid. Derivatives of this compound which have substituents at 3 are named 7-amino-3-R-decephalosporanic acid.

The above structural formulas can also be written using the following conventions to distinguish the stereoconfiguration, e.g.,

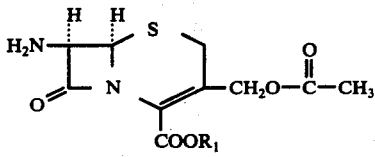

In the compound above, the dotted lines connecting the two hydrogen atoms to the ring indicate that the hydrogen atoms are down from the plane of the β-lactam ring; the straight line connecting the nitrogen indicates that it is up from the plane of the ring. Accepted usage in the cephalosporin art assumes this configuration when configuration is not indicated; this is because this configuration is that of the "normal" of biologically active cephalosporin, as produced by fermentation processes.

There is another possible steric configuration for a cephalosporin, e.g.,

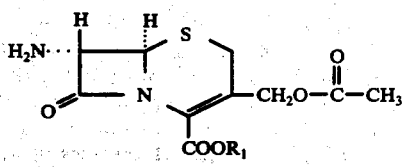

In this formula, the nitrogen and the hydrogen at position 6 is α, or down from the ring; the hydrogen at position 7 is β, or up from the ring. This type of configuration is termed "epi" cephalosporin.

Although these examples are given using the cephalosporin nucleus, it is apparent that the basic penicillin-type nucleus can be discussed in a similar fashion, e.g.,

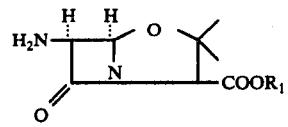

which is the normal oxa-dethia penicillin epimer.

It is clear that all these steric conventions are not absolute representations, but common usage has accepted that of formula I as "normal" and has accepted the α, β namenclature, and the dotted vs. straight lines as indicating the biologically active cephalosporin. This convention is used for all cephalosporin derivatives having substituents at either of the two positions available at carbon 7, as well as for penicillin derivatives substituted at carbon 6.

As has been stated, when naturally occurring cephalosporin or penicillin is employed, it is in the "normal" configuration. However, during the course of chemical reactions, or if the compound is prepared by total synthesis, the products are obtained in mixtures of "normal" and "epi" or as the "epi" configuration. More specifically, others in the same laboratories of the inventor have completed work on a total synthesis procedure which yields chiefly the epi, or 7α-amino compounds, of formula II. In order to yield active and commercially valuable antibiotics, it has been necessary to provide a route to "epimerize" (meaning change the configuration) the "epi" cephalosporin to the "normal" cephalosporin.

It is, therefore, a purpose of this invention to provide an epimerization procedure to convert the epi cephalosporin or penicillin to the normal form. (In this connection, it is noted that it is unnecessary to specify the configuration of both substituents on the 7-(or 6-) carbon; if the nitrogen configuration is indicated, the other substituent, i.e., the hydrogen, is obviously the other configuration.) It is an additional object of the invention to provide the desirable "normal" cephalosporins or penicillins in high yield, whether the starting material is pure "epi" material, or a mixture of epi and normal.

It is yet another object of this invention to provide an alternative epimerization route to produce the "normal" compound in high yield.

The following flow sheet and diagram is pertinent to the epimerization procedure.

FLOW SHEET I

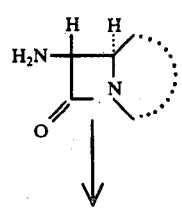

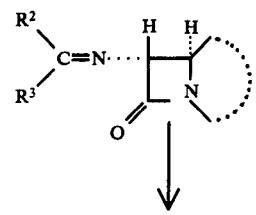

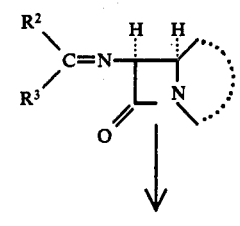

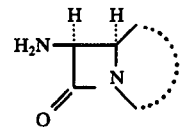

The novel process of this invention starts with the α-amino compound II, the dotted line indicates the group of substituents herein defined. This is reacted to form the aldimino or Schiff's base group. The aldimino group is prepared by reacting a suitable aldehyde or ketone with the amino group. Particularly preferred are aromatic aldehydes, substituted or unsubstituted, having 1, 2, or 3 aromatic rings, such as those derived from benzene or naphthalene. One or more substituents are possible in the aromatic aldehyde, including $C_1$ to $C_3$ alkyl (e.g., methyl, ethyl, propyl, isopropyl), $C_1$ to $C_3$ alkoxy (e.g., methoxy, ethoxy, propoxy, etc.), cyano, nitro, hydroxy, halogen (e.g., chlorine, fluorine, bromine, or iodine), trifluoromethyl, carboxy, amino, $C_1$ to $C_4$ carboxyalkyl (e.g., carboxymethyl, carboxyl ethyl, etc.), sulfonyl and carboxy derivatives such as esters, amides or the like.

Representative of the above aromatic aldehydes are benzaldehyde, napthaldehyde, salicylaldehyde, m-tolualdehyde, o-tolualdehyde, o-chlorobenzaldehyde, o-methoxybenzaldehyde, p-nitrobenzaldehyde, p-chlorobenzaldehyde, m-hydroxybenzaldehyde, 2-hydroxynaphthaldehyde, as well as others.

Also suitable are aliphatic aldehydes, or ketones including those having 1–10 carbon atoms as well as substituted aliphatic aldehydes and ketones; the optional substituents can be those mentioned in discussing the aromatic aldehydes. Representative are acetone, hexafluoroacetone, chloral, ethoxyacetaldehyde, trimethylacetaldehyde, and others.

In the compounds of formulas III and IV, $R^2$ represents the aromatic or aliphatic fragment of the aldehyde $R^3 = H$) or ketone ($R^3 =$ alkanoyl) attached to the imino linkage

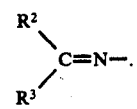

The starting material II and the chosen aldehyde or ketone are mixed together in approximately equimolar amounts in an inert solvent. Suitable solvents are ethanol, dioxane, acetonitrile, dimethylformamide, dimethylsulfoxide, benzene, toluene, methylene chloride, chloroform, ethyl acetate, and the like. The reaction proceeds readily at temperatures ranging from ambient to reflux temperature of the solvent. Since this condensation is an equilibrium reaction and since water is one of the products of the reaction, water can be removed from active participation in further reactions by any of a number of usual methods, including azeotropic distillation, molecular sieves, chemical entrapment using potassium carbonate, magnesium sulfate, etc., or borate esters. The particular method is dependent upon the exact parameters of the reaction. The reaction is terminated by evaporation of the solvent. The α-imino derivative III is then recovered and used in the next step.

The compound III is then dissolved in an inert aprotic solvent, or a mixture of two or more such solvents. The requirement that the solvent be aprotic is critical to maintain the ultimate high yield of the desired cephalosporin. This type of solvent is well known to those skilled in the art, and many suitable solvents are commercially available. Included are any solvents having no free proton source, and inert to reaction with the cephalosporin or any subsequent reactants. Included are ethers, glycols, polyethylene glycols having terminal methoxy groups, amines, hydrocarbon solvents, or others. Included are such solvents as tetrahydrofuran, dioxane, acetonitrile, benzene, ether, glyme, diglyme, pyridine, and others.

An equivalent or more of a strong base is then added. The addition of the strong base is the critical step in this process. Many bases can be used; the important characteristic is the basicity of the base (the $Pk_b$ value) as compared to the basicity (or $Pk_b$) of the aldimino compound III is the one resulting from the leaving of the hydrogen atom). It is not necessary to assign specific limits to these $Pk_b$ values; it is significantly greater than of the anion, such that in the presence of the strong base, the aldimino compound II is principally converted into its anionic form. These conversions are most easily monitored visually, since we have found that there is generally a perceptible color change between the aldimino compound and its anionic form, and correspondingly between the "epi" and the "normal" form. Moreover, by use of nuclear magnetic resonance techniques, the color identity of the various thermodynamic forms of the cephalosporin can be postulated. It is cautioned that the deepest most intense colorations are dependent upon the identity both of the aldehyde and the cation of the strong base, e.g., thus for a deep blue-green shift is observed when the aldehyde is p-nitro benzaldehyde an lithium compounds, particularly phenyl lithium is used. This base can be either organic or inorganic. Particularly preferred are organosodium, organopotassium, or organolithium compounds, including aryllithiums, sodiums or potassiums such as phenyl lithium or tolyllithium. Substituted aryl metallolithium compounds can also be used. Alkylmetallo compounds wherein alkyl can be straight or branched having 1-6 carbon atoms are also useful, such as methyllithium, n-butylsodium, t-butyllithium, ethylpotassium, hexylsodium, n-butyllithium. Metallo alkylamides or dialkylamides wherein alkyl is ether straight or branched having 1-6 carbon atoms, e.g., lithium diisopropylamide, are also useful.

In addition, lithium, sodium, or potassium t-butoxide, or other bases such as di-t-butylpotassium phenoxide, or N-lithio succinimide, or the sodium, lithium, or potassium hydrides can be used.

The strong base functions as an "activating agent". It is added to the solution of compound III at a low temperature (from about −200 to 20° C. and preferably −100° to 10° C., most preferably between about −100° and −60° C.), preferably under an inert atmosphere. The amount of activating agent employed is from 1–3 equivalent weights, which is usually sufficient to produce a strong color change in the solution. The color is an indicator that the activated form of compound III is present, although a visible color change is not necessarily produced in every reaction.

It is noted here that although the strong base can be added directly to the solution of compound III, it can also be prepared in situ. The metalloamides are particularly suitable for this procedure, i.e., by dissolving, e.g., methyllithium, then adding, e.g., diisopropylamine and stirring.

Following addition of a strong base, a co-solvent, which is a dipolar aprotic solvent is added to the mixture. By the term "dipolar aprotic solvent" I mean a strongly dipolar solvent having no acidic proton which will complex with the cation of the strong base. Those skilled in the art will recognize that this definition of the "co-solvent" overlaps chemically with that of the "solvent". This overlap is intentional; I have found that, in many cases, the so-called "co-solvent", that is, the "dipolar aprotic solvent" can be used as the only solvent or reaction. Therefore, I favor the use of two sequential solvents as an optional step, if a dipolar aprotic solvent is used from beginning of the reaction. Note however, that the criticality is of the aprotic nature of the solvent, which is met in any case.

Operable co-solvents include tetramethylethylene diamine; 1,2-dimethoxyethane; 2-methoxyethanol; the family of polyethylene glycols having terminal methoxy groups; known generically as "polyglymes, i.e., glyme, diglyme, triglyme, pentaglyme, hexaglyme, and the "crown ethers", or cyclized polyglymes. Preferred solvents also include dimethylformamide, dimethylsulfoxide, hexamethylphosphoramide, N-methyl pyrrolidine, or dimethylacetamide.

The solvent and the co-solvent are preferably employed sequentially, as described, although this is not critical; the solvent, co-solvent, and strong base, can operably be added in any order to the α-imino compound, III.

Following the addition of the solvent, base, and co-solvent to the α-imino compound, a molecular excess (from 1-5 equivalents) of an acid is added in one addition as quickly as possible. The acid employed can be any organic or inorganic acid; the only limitation is that it not affect the cephalosporin ring. Preferably, a lower carboxylic acid is employed having 1-5 carbon atoms; most preferably, acetic acid is used when a carboxylic acid is used; it can be added as an aqueous solution or in the presence of water. The acid serves as a source of protons which exist as solvated protons in the reaction solution.

After the acid has been added, the compound IV, the β-imino compound, is present in the reaction mixture. This can be isolated using standard purification techniques.

The β-imino compound IV can then be regenerated to the β-imino compound I. This process utilizes the reaction of IV with an amine in the presence of an acid catalyst. The amine employed can be aniline, hydrazine, or hydrazine derivatives such as phenylhydrazine, 2,4-dinitrophenylhydrazine, and the like. The acid catalyst can be any commonly used strong organic or inorganic acid such as hydrochloric acid or p-toluene sulfonic acid. One preferable combination utilizes aniline hydrochloride, which serves as both acid and amine. Another preferred combination is 2,4-dinitrophenyl hydrazine and p-toluene sulfonic acid. The reaction conditions of the regeneration are chosen such that no undesired hydrolysis or ring damage occurs, and is preferably carried out in a lower alkanol medium (1–5 carbon atoms), such as methanol, ethanol, and the like, although other solvents including dimethoxyethane or dimethylformamide may also be used. The temperature is that of the surroundings. The relative amounts of acid and amine employed depends on the specific aldehyde and amine used, since the regeneration involves an equilibrium. The choice of amounts of the reagents is within the skill of one in the art.

The above reaction conditions are suitable for removal of difficult hydrolyzable Schiff's bases, such as those with strong electronegative groups. When the Schiff's base was formed, e.g., with benzaldehyde, the following methods can also be used to regenerate the amine.

The β-imino compound can be dissolved in ether, and then added slowly to an ether solution of p-toluene sulfonic acid. No additional amine is needed. The formed salt will either crystallize or oil out of solution. Following removal of the ether by decanting or the like, the tosylate salt is treated with aqueous pH 8.0 solution and extracted to recover the desired 7β-amino compound.

An alternate route involves treatment of the β-imino compound with pH 2–2.5 buffer for 5–15 minutes, extracting with ether to remove the free aldehyde, then neutralizing to pH 8.0 and extracting to recover the β-amino compound I.

As referred to earlier an alternative route to epimerization is also provided herein. This route involves the use of the same starting material, compound II, and passes through the same aldimino compound III, as in Flow Sheet I. However, the process conditions are different from those of the first process, since the latter is thermodynamically a true "epimerization" process; the process now under discussion is more correctly termed "equilibration" process. The use of the term "equilibration" signifies that a thermodynamic equilibrium resulting in the preparation of a certain percentage of the normal form admixed with a certain percentage of epi form. By contrast, the epimerization procedure yields primarily the normal compound. For ease of differentiation between the two processes, this alternative route will be called an equilibration process henceforth.

After formation of the aldimino compound III, it is dissolved in an inert solvent. The class of solvents is less restrictive than the solvent employed in the epimerization reaction. So the solvents employed therein can also be used here; in addition, common solvents such as dimethylformamide; acetonitrile, dimethylsulfoxide, HMPA, acetone, isopropanol, tertiarybutylalcohol, chloroform, carbontetrachloride, methylenechloride, nitromethane, and others.

After, a base is added to the reaction mixture; this base can be any moderately strong base. Particularly preferred are hindered amines, such as tertiaryamines. Secondary or primary amines which will not attack the betalactone ring are also operable. These compounds include diisopropylethylamine, triethylamine, diisopropylamine, 2,6-lutidine, o-di-t-butyl pyridine, dimethylethylamine diazobicyclononane, diazobiscycloundecane, 1,8-bis(dimethylamino)naphthalene, or diazobicyclooctane, and others.

In some cases, it has been found that only a small amount of the base, even a catalytic amount, will be needed for the reaction.

The temperature for this equilibration reaction can be between about −150° C. or below to about 50° C. Preferred is between about −20° C. to about −25° C.

The equilibration reaction occurs when all components are admixed; the normal, compound IV, is present in the reaction mixture almost immediately, and generally within 1–3 hours at the lower temperatures. It is isolated and regenerated to the amino compound I substantially as described above.

All the compounds described in Flow Sheet I, since they result from a total synthesis procedure, are racemic mixtures of both d- and l-forms. The separation of the two optically active components can be conveniently done at the end of the synthesis indicated, i.e., when the compound of formula I is obtained. Alternatively, the compound of formula I can be acylated to yield d,l-7β-acylamino cephalosporins, and then separated using readily available processes. For example, resolution can be accomplished by reaction with an optically active base, separation of the resulting diastereomers, and reconversion of the diastereomers to the free acid or a salt thereof.

The starting compounds of formula II, as has been stated, are prepared by a total synthesis method which does not form part of the present invention.

The total synthesis is disclosed and claimed in a series of United States pending applications, all filed in the names of Burton G. Christensen and Ronald W. Ratcliffe, and assigned to Merck & Co., Inc.

Starting materials of formula IIA are disclosed and claimed in U.S. application Ser. No. 244,271, filed Apr. 14, 1972, now abandoned, continuations-in-part of which are U.S. application Ser. No. 267,845, filed June 30, 1972; now abandoned U.S. application Ser. No. 267,846, filed June 30, 1972; now abandoned, U.S. application Ser. No. 296,356, filed Oct. 10, 1972; now abandoned, and U.S. application Ser. No. 336,561, filed Mar. 5, 1973.

Starting materials of formula IIB are disclosed and claimed in U.S. application Ser. No. 303,905, filed Nov. 6, 1972, now abandoned, a continuation-in-part of which is U.S. application Ser. No. 395,662, filed Sept. 18, 1973 now abandoned.

Starting materials of formula C and D are disclosed and claimed in U.S. application Ser. No. 306,064, filed Nov. 13, 1972, now abandoned continuations-in-part of which are U.S. application Ser. No. 314,485, filed Dec. 12, 1972; now abandoned and U.S. application Ser. No. 392,159, filed Aug. 27, 1973 now U.S. Pat. No. 3,947,413.

Starting materials of formula IIE are disclosed and claimed in U.S. application Ser. No. 319,946, filed Dec. 29, 1972; now abandoned and its continuation-in-part, U.S. application Ser. No. 410,831, filed Nov. 8, 1973.

Starting materials of formula IIF are disclosed and claimed in U.S. application Ser. No. 340,802, filed Mar. 13, 1973, now abandoned a continuation-in-part of which is U.S. Ser. No. 397,516, filed Sept. 17, 1973 now abandoned.

The following examples illustrate the processes of this invention. It is noted that in addition to the total synthesis described, any method can be used to prepare the 7α-amino cephalosporin or 6α-aminopenicillin. Also, this inventive method can be used to epimerize any α-amino cephalosporin or penicillin obtained through isolation of a fermentation process, chemical reactions on naturally produced compounds, or any total synthesis process.

EXAMPLE 1 p-Methoxybenzyl dl-7β-amino-3-acetoxymethyl-3-cephem-4-carboxylate

Step A: p-Methoxybenzyl dl-7α-(p-nitrobenzylideneamino)-cephalosporanate

A mixture of p-methoxybenzyl dl-7α-aminocephalosporanate (134 mg., 0.34 mMol), p-nitrobenzaldehyde (47 mg., 0.31 mMol), magnesium sulfate (800 mg.), and methylene chloride (8 ml.) is stirred in a capped flask for 13 hours at room temperature. The mixture is filtered and the filtrate is evaporated under reduced pressure to give a yellow gum. The crude product is three times dissolved in benzene and evaporated in vacuo to give p-methoxybenzyl dl-3-acetoxymethyl-7α-(p-nitrobenzylideneamino)-3-cephem-4-carboxylate (163 mg.) as a yellow solid: ir (CHCl$_3$) 5.61, 5.76, 6.10, 6.21, 6.59, 7.41, 8.04 and 9.64μ; mnr (CDCl$_3$)λ7.95 (s, 3, C$\underline{H}_3$CO), 6.67, 6.28 (dd, 2, J=18Hz, 2-C$\underline{H}_2$), 6.18 (s, 3, ArOC$\underline{H}_3$), 5.22, 4.93 (dd, 2, J=13Hz C$\underline{H}_2$OAc), 5.08 (d, 1, J=2H$_z$, H6). 4.72 (d, 1, J=2Hz, H7), 4.66 (s, 2, ArC$\underline{H}_2$), 3.10, 2.60 (dd, 4, J=9Hz, MeOAr$\underline{H}$), 2.05, 1.63 (dd, 4, J=9Hz, O$_2$NAr$\underline{H}$), and 1.41 (s, 1, —C$\underline{H}$=M—).

Step B: p-Methoxybenzyl dl-7β-(p-nitrobenzylideneamino)-cephalosporanate

A solution of p-methoxybenzyl dl-3-acetoxymethyl-7α-(p-nitrobenzylideneamino)-3-cephem-4-carboxylate (163 mg., 0.31 mMol) in dry tetrahydrofuran (4.8 ml.) is purged with nitrogen and cooled in a dry ice-acetone bath. Phenyl lithium (135 μl. of a 2.3 M solution in 7:3 benzene-ether) is added rapidly via syringe to give an inky blue solution. Dimethylformamide (6 ml.) is added dropwise over a period of 4 minutes to the reaction mixture. After stirring an additional 1 minute at −78° C., the reaction mixture is quenched with a solution of water (56 μl., 3.1 mMol) and acetic acid (44 μl., 0.77 mMol) in tetrahydrofuran (4.8 ml.). The mixture is allowed to warm to room temperature, then diluted with benzene (100 ml.) and washed with water (6 × 40 ml.). The second wash is acidified with pH 3.0 phosphate buffer (1 ml. of a 1 M solution) and the fifth basified with pH 9.0 phosphate buffer (1 ml. of a 1 M solution). The organic phase is dried over magnesium sulfate, filtered, and evaporated under reduced pressure to give a 3:2 mixture of p-methoxybenzyl dl-3-acetoxymethyl-7α-(p-nitrobenzylideneamino)-3-cephem-4-carboxylate and p-methoxybenzyl dl-3-acetoxymethyl-7β-(p-nitrobenzylideneamino)-3-cephem-4-carboxylate as an orange oil (149 mg.). The 7β-isomer shows characteristic bands in the nmr spectrum at 4.58 (d of d, J=2Hz and J=5Hz, H7) and 1.33 (d, J=2Hz, —CH=N—).

Step C: p-Methoxybenzyl dl-7β-amino-3-acetoxymethyl-3-cephem-4-carboxylate 2,4-Dinitrophenylhydrazine (55.5 mg., 0.28 mMol) is added to a stirring solution of p-toluenesulfonic acid monohydrate (53.3 mg., 0.28 mMol) in ethanol (8 ml.). The resulting mixture is stirred for 45 minutes at room temperature, then treated with a solution of p-methoxybenzyl dl-3-acetoxymethyl-7α-(p-nitrobenzylideneamino)-3-cephem-4-carboxylate and p-methoxybenzyl dl-3acetoxymethyl-7β-(p-nitrobenzylideneamino)-3-cephem-4-carboxylate (3:2 mixture, 147 mg., 0.28 mMol) in chloroform (1 ml.). After stirring for 30 minutes at room temperature, the reaction mixture is filtered and the filtrate is evaporated in vacuo. The residue is diluted with 1 M dipotassium hydrogen phosphate (0.6 ml.) and water (4 ml.) and extracted with ether (3 × 10 ml.). The combined extracts are washed with water (10 ml.) and saturated brine (15 ml.), dried over magnesium sulfate, filtered, and evaporated in vacuo to yield a 3:2 mixture of p-methoxybenzyl dl-3-acetoxymethyl-7α-amino-3-cephem-4-carboxylate and p-methoxybenzyl dl-3-acetoxymethyl-7β-amino-3-cephem-4-carboxylate as an orange oil (101 mg.).

Step D: p-Methoxybenzyl dl-7β-(p-nitrobenzylideneamino)-cephalosporanate (alternate route)

One gram of p-methoxybenzyl dl-7α-(p-nitrobenzylideneamino)cephalosporanate (from Step A, Example 1) is dissolved in 20 ml. methylene chloride and treated with 0.5 g. DBN (diazabicyclononane) for 10 minutes at room temperature, establishing the equilibrium between the two epimers. The solution is washed with aqueous pH 3.0 phosphate, then water, and then dried with MgSO$_4$. After filtration and evaporation of the solvent, a mixture of epimers is obtained. Although the alpha form predominates in this mixture, the pure beta can be isolated by chromatography on silica gel, eluting with 4:1 chloroformethyl acetate, and used as described above.

EXAMPLE 2 p-Methoxybenzyl dl-7β-amino-3-methyl-3-cephem-3-carboxylate

Step A: p-Methoxybenzyl dl-7α-(p-nitrobenzylideneamino)-3-methyl decephalospornate In like manner to that of Example 1, Step A, p-methoxybenzyl dl-7α-amino-3-methyl cephalosporanate is converted into compound p-methoxybenzyl dl-7α-(p-nitrobenzylideneamino)-3-methyl decephalosporanate, identified by NMR: (δ, CDCl$_3$) 2.15 (3—CH$_3$), 3.1, 3.4, 3.55, 3.85 (SCH$_2$), 4.19 (7—H), 5.0 (6—H), 7.9, 8.05, 8.4, 8.55, (C$_6$H$_4$NO$_2$), 8.65 (CH=N).

Step B: p-Methoxybenzyl dl-7β-(p-nitrobenzylideneamino)-3-methyl decephalosporanate p-Methoxybenzyl dl-7α-(p-nitrobenzylideneamino)-3-methyl decephalosporanate is isomerized into a 2:1–3:1 mixture of compounds p-methoxybenzyl dl-7β-(p-nitrobenzylideneamino)-3-methyl decephalosporanate and p-methoxybenzyl dl-7α-(p-nitrobenzylideneamino)-3-methyl decephalosporanate using the process described in Example 1, Step B. The desired 7β-epimer is distinguished from the 7α-compound in the NMR by having 7-H shifted to 5.35, 5.45δ, 6-H shifted to 5.1, 5.2δ, and CH=N shifted to 8.75δ.

Step C: p-Methoxybenzyl dl-7β-amino-3-methyl decephalosporanate p-Methoxybenzyl dl-7β-(p-nitrobenzylideneamino)-3-methyl decephalosporanate is converted into compound p-methoxybenzyl dl-7β-amino-3-methyl decephalosporanate, using the method described in Example 1, Step C; the product has an IR spectrum (film) 3.0, 5.65, 5.80μ. MS 228.

EXAMPLE 3

2,2,2-Trichloroethyl d,1-7β-amino-3-methoxymethyloxymethyl-3-cephem-4-carboxylate Step A: 2,2,2-Trichloroethyl d,1-7α-benzylideneamino-3-methoxymethyloxymethyl-3-cephem-4-carboxylate A mixture of 2,2,2-trichloroethyl d,1-7α-amino-3-methoxymethyloxymethyl-3-cephem-4-carboxylate (1.18 g.) benzaldehyde (0.37 g.), and magnesium sulfate (7.50 g.) in methylene chloride (75 ml.) is stirred at room temperature for 96 hours. The mixture is filtered and the filtrate is evaporated in vacuo to an oil. This material is triturated with five portions of petroleum ether, diluted with benzene, and evaporated to give 2,2,2-trichloroethyl d,1-7α-benzylideneamino-3-methoxymethyloxymethyl-3-cephem-4-carboxylate.

Step B: 2,2,2-Trichloroethyl d,1-7β-benzylideneamino-3-methoxymethyloxymethyl-3-cephem-4-carboxylate A solution of 2,2,2-trichloroethyl d,1-7-60 -benzylideneamino-3-methoxymethyloxymethyl-3-cephem-4-carboxylate (494 mg.) in anhydrous tetrahydrofuran (15 ml.) is purged with nitrogen and cooled in a dry ice-acetone bath. Phenyl lithium (435 μl. of a 2.3 M solution in 7:3 benzene-ether) is added, giving the anion. Dimethylformamide (19 ml.) is then added dropwise over a period of 10 minutes. The reaction is quenched by addition of a solution of water (0.18 ml.) and acetic acid (0.14 ml.) in tetrahydrofuran (10 ml.). After warming to room temperature, the reaction mixture is diluted with benzene and washed six times with water. The second wash is acidified with pH 3.0 phosphate buffer and the fifth is basified with pH 9.0 phosphate buffer. The benzene solution is dried with magnesium sulfate, filtered, and evaporated in vacuo leaving a mixture of 2,2,2-trichloroethyl d,1-7α-benzylideneamino-3-methoxymethyloxymethyl-3-cephem-4-carboxylate and 2,2,2-trichloroethyl d,1-7β-benzylideneamino-3-methoxymethyloxymethyl-3-cephem-4-carboxylate.

Step C: 2,2,2-Trichloroethyl d-1-7β-3-methoxymethyloxymethyl-3-cephem-4-carboxylate 2.4-Dinitrophenyl hydrazine (172 mg.) is added to a stirring solution of p-toluenesulfonic acid monohydrate (166 mg.) in absolute ethanol (25 ml.). After having been stirred at room temperature for 45 minutes the reaction mixture is treated with 2,2,2-trichloroethyl d,1-7-benzylideneamino-3-methoxymethyloxymethyl-3-cephem-4-carboxylate (430 mg., mixture of 7α, and 7β-isomers) in a small volume of chloroform (3 ml). The mixture is stirred at room temperature for 10 minutes, filtered, and the filtrate is evaporated in vacuo. The residue is treated with 1 M dipotassium hydrogen phosphate (2 ml.) and water (15 ml.) and extracted with ether (3 × 20 ml.). The ethereal solution is dried with magnesium sulfate, filtered, and evaporated in vacuo to yield a mixture of 2,2,2-trichloroethyl d,1-7β-amino-3-methoxymethyloxymethyl-3-cephem-4-carboxylate.

EXAMPLE 4 p-Methoxybenzyl d,1-7β-amino-3-[2-(5-methyl-1,3,4-thiadiazolyl)thiomethyl]-3-cephem-4-carboxylate Step A: p-Methoxybenzyl d,1-7α-benzylideneamino-3-[2-(5-methyl-1,3,4-thiadiazolyl)thiomethyl]-3-cephem-4-carboxylate A mixture of p-methoxybenzyl d,1-7α-amino-3-[2-(5-methyl-1,3,4-thiadiazolyl)thiomethyl]-2-cephem-4-carboxylate (0.557 g.), p-nitrobenzaldehyde (0.181 g.), methylene chloride (25 ml.), and magnesium sulfate (2.50 g.) is stirred at room temperature for 15 hours. The mixture is filtered and the filtrate evaporated in vacuo to dryness. The residue is twice diluted with benzene and evaporated, affording p-methoxybenzyl d,1-7α-benzylideneamino-3-[2-(5-methyl-1,3,4-thiadiazolyl)-thiomethyl]-3-cephem-4-carboxylate.

Step B: p-Methoxybenzyl d,1-7β-benzylideneamino-3-[2-(5-methyl-1,3,4-thiadiazolyl)thiomethyl]-3-cephem-4-carboxylate A solution of p-methoxybenzyl d,1-7α-benzylideneamino-3-[2-(5-methyl-1,3,4-thiadiazolyl)thiomethyl]-3-cephem-4-carboxylate (0.688 g.) in anhydrous tetrahydrofuran (10 ml.) is cooled to −78° C. under nitrogen. Phenyl lithium (0.50 ml. of a 2.3 M solution in benzene-ether) is added rapidly with stirring. Dimethylformamide (12.5 ml.) is then added dropwise over 5 minutes. After stirring 1 more minute at −78° C., the reaction is quenched with a solution of water (0.21 ml.) and acetic acid (0.16 ml.) in tetrahydrofuran (5 ml.). The mixture is allowed to warm to room temperature, then it is diluted with benzene and washed with six portions of water. The second wash is treated with pH 3.0 phosphate buffer and the fifth with pH 9.0 phosphate buffer. The benzene solution, after being dried with magnesium sulfate, is evaporated in vacuo to yield a mixture of p-methoxybenzyl d,1-7α-benzylideneamino-3-[2-(5-methyl-1,3,4-thiadiazolyl)thiomethyl]-3-cephem-4-carboxylate and p-methoxybenzyl d,1-7β-benzylideneamino-3-[2-(5-methyl-1,3,4-thiadiazolyl)thiomethyl]-3-cephem-4-carboxylate.

Step C: p-Methoxybenzyl d,1-7β-amino-3-[2-(5-methyl-1,3,4-thiadiazolyl)thiomethyl]-3-cephem-4-carboxylate p-Methoxybenzyl d,1-7-benzylideneamino-3-[2-(5-methyl-1,3,4-thiadiazolyl)thiomethyl]-3-cephem-4-carboxylate (0.633 g., mixture of 7α- and 7β-isomers) in chloroform (5 ml.) is added to a mixture of p-toluenesulfonic acid monohydrate (0.202 g.) and 2,4-dinitrophenylhydrazine (0.210 g.) in ethanol (30 ml., mixture stirred previously for 45 minutes). After stirring 30 minutes at room temperature, the mixture is filtered and the filtrate is evaporated in vacuo to dryness. The residue is treated with water (15 ml.) containing 1 M dipotassium hydrogen phosphate (2 ml.) and extracted with ether (3 × 10 ml.). The ethereal extracts are dried with magnesium sulfate, filtered, and evaporated in vacuo. The residual oil is a mixture of p-methoxybenzyl d,1-7α-amino-3-[2-(5-methyl-1,3,4-thiadiazolyl)thiomethyl]-3-cephem-4-carboxylate and p-methoxybenzyl d,1-7β-amino-3-[2-(5-methyl-1,3,4-thiadiazolyl)thiomethyl]-3-cephem-4-carboxylate.

EXAMPLE 5 p-Bromophenacyl d,1-7β-amino-3-isobutyryloxymethyl-3-cephem-4-carboxylate

Step A: p-Bromophenacyl d,1-3-isobutyryloxymethyl-7α-(p-nitrobenzylideneamino)-3-cephem-4-carboxylate A mixture of p-bromophenacyl d,1-7α-amino-3-isobutyryloxymethyl-3-cephem-4-carboxylate (0.50 g.), p-nitrobenzaldehyde (0.15 g.), and magnesium sulfate (2.50 g.) in methylene chloride (25 ml.) is stirred in a stoppered flask for 16 hours at room temperature. The mixture is filtered and the filtrate is concentrated under reduced pressure. The residue is taken up in benzene and the solvent evaporated in vacuo. Repetition of this operation yields p-bromophenacyl d,1-3-isobutyryloxymethyl-7α-(p-nitrobenzylideneamino)-3-cephem-4-carboxylate.

Step B: p-Bromophenacyl d,1-3-isobutyryloxymethyl-7β-(p-nitrobenzylideneamino)-3-cephem-4-carboxylate p-Bromophenacyl d-1-3-isobutyryloxymethyl-7α-(p-nitrobenzylideneamino)-3-cephem-4-carboxylate (0.60 g.) is dissolved in anhydrous tetrahydrofuran (15 ml.) and the solution is cooled to −78° C. under nitrogen. One equivalent of phenyl lithium (0.41 ml. of a 2.3 M solution in 7:3 benzene-ether) is added, forming the anion. Dimethylformamide (20 ml.) is then added dropwise over 5 min. After one more minute at −78° C., a solution of water (0.17 ml.) and acetic acid (0.14 ml.) in tetrahydrofuran (10 ml.) is added. The reaction mixture is allowed to warm to room temperature; benzene (250 ml.) is added, and the solution is washed six times with water. The second wash is acidified with -nitrobenzyaldimino-2.0 phosphate buffer and the fifth basified with pH 8.0 buffer. The benzene solution is dried with magnesium sulfate, filtered, and evaporated under reduced pressure leaving a mixture of p-bromophenacyl d,1-3-isobutyryloxymethyl-7α-(p-nitrobenzylideneamino)-3-cephem-4-carboxylate and p-bromophenacyl d,1-3-isobutyryloxymethyl-7β-(p-nitrobenzylideneamino)-3-cephem-4-carboxylate.

Step C: p-Bromophenacyl d,1-7β-amino-3-isobutyryloxymethyl-3-cephem-4-carboxylate n-Bromophenacyl d,1-3-isobutyryloxymethyl-7-(p-nitrobenzylideneamino)-3-cephem-4-carboxylate (524 mg., mixture of 7α- and 7β-isomers) is dissolved in chloroform (3 ml.) and added to a solution of 2,4-dinitrophenylhydrazine p-toluenesulfonate in ethanol (prepared from 164 mg. of 2,4-dinitrophenylhydrazine and 158 mg. of p-toluenesulfonic acid monohydrate stirred in 30 ml. of ethanol previously for 45 minutes). The mixture is stirred for 30 minutes, filtered, and evaporated. The residue is treated with aqueous pH 9.2 phosphate buffer and extracted three times with ether. The ether portions are dried over magnesium sulfate, filtered, and evaporated in vacuo providing p-bromophenacyl d,1-7α-amino-3-isobutyryloxymethyl-3-cephem-4-carboxylate and p-bromophenacyl d,1-7β-amino-3-isobutyryloxymethyl-3-cephem-4-carboxylate.

EXAMPLE 6 p-Nitrobenzyl d,1-7β-amino-3-methoxymethyl-3-cephem-4-carboxylate

A mixture of p-nitrobenzyl d,1-7α-amino-3- methoxymethyl-3-cephem-4-carboxylate (0.96 g.), p-nitrobenzaldehyde (0.38 g.), magnesium sulfate (6.0 g.), and methylene chloride (60 ml.) is stirred in a capped flask at room temperature for 15 hours. This mixture is filtered and the filtrate is concentrated under reduced pressure. The residual gum is three times dissolved in benzene and evaporated in vacuo to afford p-nitrobenzyl d, 1-3-methoxymethyl-7α-(p-nitrobenzylideneamino)-3-cephem-4-carboxylate.

Step B: p-Nitrobenzyl d,1-3-methoxymethyl-7β-(p-nitrobenzylideneamino)-3-cephem-4-carboxylate A solution of p-nitrobenzyl d,1-3-methoxymethyl-7α-(p-nitrobenzylideneamino)-3-cephem-4-carboxylate (1.23 g.) in anhydrous tetrahydrofuran (35 ml.) is cooled in a dry ice-acetone bath under a nitrogen atmosphere. Phenyl lithium (1.05 ml. of a 2.3 M solution in 7:3 benzene-ether) is added rapidly with stirring to give an inky blue solution. Dimethylformamide (45 ml.) is added dropwise over a period of 10 minutes to the reaction mixture. After having been stirred an additional 1minute at −78° C., the reaction is quenched by addition of a solution of water (0.43 ml.) and acetic acid (0.35 ml.) in tetrahydrofuran (10 ml.). The reaction mixture is allowed to warm to room temperature, then diluted with benzene (500 ml.) and washed with five portions of water. The second wash is acidified with pH 3.0 phosphate buffer and the fourth basified with pH 9.0 phosphate buffer. The benzene solution is dried over magnesium sulfate, filtered, and evaporated in vacuo to give a mixture of p-nitrobenzyl d, 1-3-methoxymethyl-7α-(p-nitrobenzylideneamino)-3-cephem-4-carboxylate and p-nitrobenzyl d,1-3-methoxymethyl-7β-(p-nitrobenzylideneamino)-3-cephem-4-carboxylate.

Step C: p-Nitrobenzyl d,1-7β-amino-3-methoxymethyl-3-cephem-4-carboxylate

A mixture of 2,4-dinitrophenylhydrazine (0.482 g.) and p-toluenesulfonic acid monohydrate (0.434 g.) in ethanol (65 ml.) is stirred at room temperature for 45 minutes, then treated with a solution of p-nitrobenzyl-3-methoxymethyl-7-(p-nitrobenzylideneamino)-3-cephem-4-carboxylate (1.166 g., mixture of 7α- and 7β-isomers) in chloroform (5 ml.). After having been stirred for 30 minutes at room temperature, the reaction mixture is filtered and the filtrate is evaporated under reduced pressure. The residue is treated with water (30 ml.) and 1 M dipotassium hydrogen phosphate (4.6 ml.) and extracted with ether. The combined extracts are dried over magnesium sulfate, filtered, and evaporated to afford a mixture of p-nitrobenzyl d,1-7α-amino-3-methoxymethyl-3-cephem-4-carboxylate and p-nitrobenzyl d,1-7β-amino-3-methoxymethyl-3-cephem-4-carboxylate.

EXAMPLE 7 p-Methoxybenzyl d,1-7β-amino-3-(N,N-di-p-methoxybenzyl)-carbamoyloxymethyl-3-cephem-4-carboxylate Step A: p-Methoxybenzyl d,1-7α-(p-nitrobenzylidenamino)-3-(N,N-di-p-methoxybenzyl)carbamoyloxymethyl-3-cephem-4-carboxylate A mixture of p-methoxybenzyl d,1-7α-amino-3-(N,N-di-p-methoxybenzyl)carbamoyloxymethyl-3-cephem-4-carboxylate (2.35 g.), p-nitrobenzaldehyde (0.56 g.), magnesium sulfate (10.0 g.), and methylene chloride (100 ml.) is stirred at room temperature for 15 hours. The mixture is filtered and the filtrate is evaporated in vacuo to a gum. This material is dissolved in benzene and the solvent evaporated to yield p-methoxybenzyl d,1-7α-(p-nitrobenzylideneamino)-3-(N,N-di-p-methoxybenzyl)carbamoyloxymethyl-3-cephem-4-carboxylate.

Step B: p-Methoxybenzyl d,1-7β-(p-nitrobenzylideneamino)-3-(N,N-di-p-methoxybenzyl)carbamoyloxymethyl-3-cephem-4-carboxylate A solution of p-methoxybenzyl d,1-7α-(p-nitrobenzylideneamino)-3-(N,N-di-p-methoxybenzyl)carbamoyloxymethyl-3-cephem-4-carboxylate (0.77 g.) in anhydrous tetrahydrofuran (15 ml.) is cooled to −78° C. under nitrogen. Phenyl lithium (0.44 ml. of a 2.3 M solution in 7:3 benzene-ether) is added rapidly with stirring. Dimethylformamide (19 ml.) is then added dropwise over a period of 5 minutes. After stirring one more minute at −78° C., the reaction mixture is quenched by addition of water (0.18 ml.) and acetic acid (0.14 ml.) in tetrahydrofuran (10 ml.). The mixture is allowed to warm to room temperature. Benzene (250 ml.) is added and the solution is washed with water (6 × 100 ml.). The second wash is acidified with pH 3.0 phosphate buffer and the fifth basified with pH 9.0 phosphate buffer. The benzene solution is dried with magnesium sulfate, filtered, and evaporated in vacuo to give a mixture of p-methoxybenzyl d,1-7α-(p-nitrobenzylideneamino)-3-(N,N-di-p-methoxybenzyl)carbamoyloxymethyl-3-cephem-4-carboxylate and p-methoxybenzyl d, 1-7β-(p-nitrobenzylideneamino)-3-(N,N-di-p-methoxybenzyl)carbamoyloxymethyl-3-cephem-4-carboxylate.

Step C: p-Methoxybenzyl d,1-7β-amino-3-(N,N-di-p-methoxybenzyl)carbamoyloxymethyl-3-cephem-4-carboxylate A mixture of p-toluenesulfonic acid monohydrate (0.169 g.) and 2,4-dinitrophenylhydrazine (0.175 g.) in ethanol (25 ml.) is stirred at room temperature for 45 minutes. p-Methoxybenzyl, 1-7-(p-nitrobenzylideneamino)-3-(N,N-di-p-methoxybenzyl)carbamoyloxymethyl-3-cephem-4-carboxylate (0.675 g., mixture of 7α- and 7β-isomers) in chloroform(5 ml.) is added and the resulting mixture is stirred at room temperature for 30 minutes. The mixture is filtered and the filtrate is evaporated in vacuo. The residue is treated with 1 M dipotassium hydrogen phosphate (2 ml.) and water (13 ml.) and extracted with ether (3 × 20 ml.). The ethereal extracts are washed with water and saturated brine, dried with magnesium sulfate, filtered and evaporated in vacuo to yield a mixture of p-methoxybenzyl d,1-7α-amino-3-(N,N-di-p-methoxybenzyl)carbamoyloxymethyl-3-cephem-4-carboxylate and p-methoxybenzyl d,1-7β-amino-3-(N,N-di-p-methoxybenzyl)carbamoyloxymethyl-3-cephem4-carboxylate.

EXAMPLE 8

Sodium 7β-(and 7α)-2'-thienylacetamido)-1-methylene-1-dethiacephalosporonate

Step A: Benzyl 7α-benzaldimino-1-methylene-1-dethiacephalosporanate

Benzyl 7α-amino-1-methylene-1-dethiacephalosporanate (1.72 g.) is treated with benzaldehyde (0.55 g.). The mixture is dissolved in benzene (30 ml.) and magnesium sulfate (2.0 g.) is added. The reaction mixture is allowed to stand at room temperature for two hours. The magnesium sulfate is removed by filtration and the filtrate is evaporated to afford benzyl 7α-benzaldimino-1-methylene-1-dethiacephalosporanate.

Step B: Benzyl 7β-benzaldimino-1-methylene-1-dethiacephalosporanate

Benzyl 7α-benzaldimino-1-methylene-1-dethiacephalosporanate (1.86 g.) is dissolved in tetrahydrofuran (50 ml.) and cooled to −78° C. under nitrogen. A solution of phenyl lithium (5 ml.;1M) in benzene-ether is added dropwise over two minutes. Dimethylformamide (35 ml.) is then added over two minutes and then a mixture of water (0.09 ml.) and acetic acid (0.3 g.) in tetrahydrofuran (5.0 ml.) is added. The reaction mixture is warmed to room temperature and diluted with benzene and washed with a pH 8.0 phosphate buffer, then dried and evaporated. The residue is a mixture of the starting material and its 7β epimer at $C_7$.

Step C: Benzyl 7β-(2'-thienylacetamido)-1-methylene-1-dethiacephalosporanate and Benzyl 7α-(2'-thienylacetamido)-1-methylene-1-dethiacephalosporanate Benzyl 7-benzaldimino-1-methylene-1-dethiacephalosporanate (1.86 g.) which is a mixture of epimers at $C_7$ is dissolved in methylene chloride (35 ml.), cooled to 0° C. and treated with 2-thienylacetyl chloride (0.81 g.); pyridine (0.5 g.) is then added. After one-half hour at 0° C. water (0.5 ml.) in tetrahydrofuran (6.0 ml.) is added and the mixture is stirred vigorously for one-half hour. The reaction mixture is washed once with a ph 8.0 buffer, then dried and evaporated. The residue is chromatographed on silica gel to afford benzyl 7β-(2'-thienylacetamido)-1-methylene-1-dethiacephalosporanate and benzyl 7α-(2'-thienylacetamido)-1-methylene-1-dethiacephalosporanate.

Step D: Sodium 7β-(and 7α)-(2'-thienylacetamido)-1-methylene-1-dethiacephalosporanate Benzyl 7β-(2-thienylacetamido)-1-methylene-1-dethiacephalosporanate (0.300 g.) is dissolved in ethanol (15 ml.), water is added to turbidity and then 0.300 g. of the catalyst (10% Pd/C) is added. The mixture is reduced under hydrogen at 40 atm. for one-half hour. The catalyst is filtered off. The filtrate is evaporated under reduced pressure to remove most of the ethanol and then treated with sodium bicarbonate (0.1 g.) and the solution is freeze-dried to afford sodium 7β-(2'-thienylacetamido)-1-methylene-1-dethiacephalosporanate. Treatment of benzyl 7α-(2'-thienylacetamido)-1-methylene-1-dethiacephalosporanate under the above conditions gives the sodium 7α(2-thienylacetamido)-1-methylene-1-dethiacephalosporanate.

EXAMPLE 9

Benzyl 7β-amino-1-oxadethiacephalosporanate

Step A: Benzyl 7α-(p-Nitrobenzaldimino)-1-oxadethiacephalosporanate

Benzyl 7α-amino-1-oxadethiacephalosporanate, 350 mg., in 15 ml. methylene chloride, is treated with 2 g. $MgSO_4$ and 0.95 equivalent of p-nitrobenzalehyde. After two houtrs' stirring at room temperature, the solution is filtered and evaporated, affording 570 mg. of benzyl dl-7α-(p-nitrobenzaldimino)-1-oxadethiacephalosporanate, identified by NMR.

Step B: Benzyl 7β-(p-Nitrobenzaldimino)-1-oxadethiacephalosporanate

Benzyl dl-7α-(p-nitrobenzaldimino)-1-oxadethiacephalosporanate, 48 mg., is dissolved in 2 ml. tetrahydrofuran and cooled to −78° C. One equivalent of phenyl lithium, 2M, is added, forming the deep blue anion. DMF, 2.5 ml., is added, and after one more minute at −78° C., a solution of 23 microliters water and 18 microliters of acetic acid AcOH in 2 ml. tetrahydrofuran is added. The reaction mixture is allowed to warm to room temperature, 40 ml. benzene is added, and the solution is washed with water six times. The second wash is acidified with pH 2.0 phosphate buffer, and the fifth with pH 8.0 buffer. The benzene solution is dried with $MgSO_4$, filtered and evaporated, leaving an oil which consists of about a 3:1 mixture of benzyl dl-7β-(p-nitrobenzamdimino)-1-oxadethiacephalosporanate to benzyl dl-7α-(p-nitrobenzaldimino)-1-oxadethiacephalosporanate.

Step C: Benzyl dl-7β-amino-1-oxadethiacephalosporanate

Benzyl dl-7β-(p-nitrobenzaldimino)-1-oxadethiacephalosporanate, 49 mg., is dissolved in 0.5 ml. chloroform and added to a solution of 2,4-dinitrophenylhydrazine p-toluensulfonic acid in 5 ml. ethanol (prepared from 27 mg. 2,4-dinitrophenylhydrazine and 26 mg. p-toluenesulfonic acid stirred in ethanol previously for 45 minutes). The mixture is stirred 30 minutes, filtered and evaporated. The residue is treated with aqueous pH 8.0 buffer and extracted three times with ether. The ether portions are dried with $MgSO_4$, filtered and evaporated, providing the compound benzyl dl-7β-amino-1-oxadethiacephalosporanate.

EXAMPLE 10

Benzyl 7β-amino-1-benzylamino-dethia-3-acetoxymethyl-3-cephem-4-carboxylate

Step A: Benzyl 7α-p-nitrobenzaldimino-1-benzylaminodethiacephalosporanate

To a solution of 152 mg. (1 mmole) of p-nitrobenzaldehyde in 4 ml. of chloroform is added a solution of 435 mg. (1 mmole) of benzyl 7α-amino-1-benzylaminodethiacephalosporanate in 6 ml. of chloroform. 1.5 g. of anhydrous magnesium sulfate is added and the mixture is stirred for 2 hours. The solid is filtered and washed with chloroform. The solvent removal from the filtrate gives benzyl7α-p-nitrobenzaldimino-1-benzylamino-dethiacephalosporanate.

Similarly, condensation of benzyl 7α-amino-1-methylaminodethiacephalosporanate with p-nitrobenzaldehyde gives benzyl 7α-p-nitrobenzaldimino-1-methylamino-dethiacephalosporanate.

Step B: Benzyl 7α-p-nitrobenzaldimino-1-benzylaminodethiacephalosporanate and benzyl 7β-nitrobenzyladimino-1-benzylamino-dethiacephalosporanate To a solution of 523 mg. of benzyl 7α-p-nitrobenzaldimino-1-benzylamino-dethiacephalosporanate in 10 ml. of anhydrous tetrahydrofuran is added under nitrogen 0.435 ml. of 2.3M solution of phenyl lithium at −78° C. 10 ml. of N,N-dimethylformamide is slowly added followed by a mixture of 30 μl. of water and 76 μl. of glacial acetic acid in 2 ml. of tetrahydrofuran. The reaction mixture is let to warm to room temperature, diluted with benzene and washed with water and brine. Evaporation of the solvent gives a mixture of the starting material and its $C_7$ epimer.

Similarly, a mixture of starting Schiff base and its epimer at $C_7$ is obtained from benzyl 7α-p-nitrobenzaldimino-1-methylamino-dethiacephalosporanate.

Step C: Benzyl 7α-amino-1-benzylamino-dethiacephalosporanate and benzyl 7β-amino-1-benzylaminodethiacephalosporanate To a solution of 198 mg. (1 mmole) of 2,4-dinitrophenylhydrazine in 10 ml. of ethanol is added 190 mg. (1 mmole) of p-toluensulfonic acid monohydrate and the mixture is allowed to stir for 0.5 hour at room temperature. A solution of 523 mg. (1 mmole) of benzyl-7-p-nitrobenzaldimino-1-benzylamino-dethiacephalosporanate ($C_7$ α and β epimeric mixture) in 10 ml. of ethanol is then added. The reaction mixture is stirred for 0.5 hour at room temperature, filtered and the filtrate evaporated. The residue is taken up in 100 ml. of methylene chloride, washed with 2 × 50 ml. of brine, dried over anhydrous magnesium sulfate and evaporated to give benzyl-7-amino-1-benzylamino-dethiacephalosporanate (α and β epimers at $C_7$).

Similarly, $C_7$ epimeric mixture of benzyl-7-amino-1-methylamino-dethiacephalosporanate is obtained from benzyl-7-p-nitrobenzaldimino-1-methylamino-dethiacephalosporanate (mixture of α and β epimers at $C_7$).

EXAMPLE 11 p-Methoxybenzyl dl-3-phenyl-7β-amino-3-cephem-4-carboxylate

Step A: p-Methoxybenzyl dl-3-phenyl-7α-(p-nitrobenzylideneamino)-3-cephem-4-carboxylate p-Methoxybenzyl dl-3-phenyl-b 7α-amino-3-cephem-4-carboxylate (101 mg.) is treated with 36 mg. p-nitrobenzaldehyde and 0.7 g. of magnesium sulfate in 5 ml. of methylene chloride with stirring for 2 hours. The solution is filtered and evaporated to afford 133 mg. p-methoxybenzyl dl-3-phenyl-7α-(p-nitrobenzylideneamino)-3-cephem-4-carboxylate.

NMR ($CDCl_3$): C$\underline{H}$=N at 8.55 δ.

When p-methoxybenzyl dl-3-p-chlorophenyl-7α-amino-3-cephem-4-carboxylate, p-methoxybenzyl dl-3-p-cyanophenyl-7α-amino-3-cephem-4-carboxylate, p-methoxybenzyl dl-3-p-carbomethoxyphenyl-7α-amino-3-cephem-4-carboxylate, p-methoxybenzyl dl-3-(4-pyridyl)-7α-amino-3-cephem-4-carboxylate, p-methoxybenzyl dl-3-(2-furyl)-7α-amino-3-cephem-4-carboxylate and p-methoxybenzyl dl-3-(5-methyl-2-furyl)-7α-amino-3-cephem-4-carboxylate are used in place of p-methoxybenzyl dl-3-phenyl-7α-amino-3-cephem-4-carboxylate in the above-described process, p-methoxybenzyl dl-3-p-chlorophenyl-7α-(p-nitrobenzylideneamino)-3-cephem-4-carboxylate, p-methoxybenzyl dl-3-p-cyanophenyl-7α-(p-nitrobenzylideneamino)-3-cephem-4-carboxylate, p-methoxybenzyl dl-3-p-carbomethoxyphenyl-7α-(p-nitrobenzylideneamino)-3-cephem-4-carboxylate, p-methoxybenzyl dl-3-(4-pyridyl)-7α-(p-nitrobenzylideneamino)-3-cephem-4-carboxylate, p-methoxybenzyl dl-3-(2-furyl)-7α-(pnitrobenzylideneamino)-3-cephem-4-carboxylate and p-methoxybenzyl dl-3-(4-methyl-2-furyl)-7α-(p-nitrobenzylideneamino)-3-cephem-4-carboxylate are obtained.

The p-methoxybenzyl dl-3-p-carbomethoxyphenyl-7α-(p-nitrobenzylideneamino)-3-cephem-4-carboxylate prepared by this process has the following characteristics. NMR (δ, $CDCl_3$): 8.60 (CH=N), other peaks correct.

Step B: p-Methoxybenzyl dl-3-phenyl-7β(p-nitrobenzylideneamino)-3-cephem-4-carboxylate p-Methoxybenzyl dl-3-phenyl-7α(p-nitrobenzylideneamino)-3-cephem-4-carboxylate (130 mg.) is dissolved in 4 ml. tetrahydrofuran. At −78° C. under nitrogen, 0.163 ml. 2.3 M phenyl lithium is added, forming the 7-lithium derivative of p-methoxybenzyl dl-3-phenyl-7α-(p-nitrobenzylideneamino)-3-cephem-4-carboxylate. Dimethylformamide (5 ml.) is added, and then a mixture of 3 ml. tetrahydrofuran, 0.063 ml. of acetic acid and 0.020 ml. of water. The reaction mixture is warmed to room temperature, diluted with 50 ml. benzene and washed 6 times with water. Wash no. 2 contains pH 2.0 phosphate buffer, and wash no. 5 pH 8.0 phosphate buffer. After drying with magnesium sulfate, filtration and evaporation of the solvent, a 2:1 mixture of p-methoxybenzyl dl-3-phenyl-7β-(p-nitrobenzylideneamino)-3-cephem-4-carboxylate and p-methoxybenzyl dl-3-phenyl-7α-(p-nitrobenzylideneamino)-3-cephem-4-carboxylate are obtained in substantially quantitative yield. The NMR of p-methoxybenzyl dl-3-phenyl-7β-(p-nitrobenzylideneamino)-3-cephem-4-carboxylate shows C$\underline{H}$=N at 8.70 δ.

When p-methoxybenzyl dl-3-p-chlorophenyl-7α-(p-nitrobenzylideneamino)-3-cephem-4-carboxylate, p-methoxybenzyl dl-3-p-cyanophenyl-7α-(p-nitrobenzylideneamino)-3-cephem-4-carboxylate, p-methoxybenzyl dl-3-p-carbomethoxyphenyl-7α-(p-nitrobenzylideneamino)-3-cephem-4-carboxylate, p-methoxybenzyl dl-3-(4-pyridyl)-7α-(p-nitrobenzylideneamino)-3-cephem-4-carboxylate, p-methoxybenzyl dl-3-(2-furyl)-7α-(p-nitrobenzylideneamino)-3-cephem-4-carboxylate and p-methoxybenzyl dl-3-(5-methyl-2-furyl)-7α-(p-nitrobenzylideneamino)-3-cephem-4-carboxylate are used in place of p-methoxybenzyl dl-3-phenyl-7α-(p-nitrobenzylideneamino)-3-cephem-4-carboxylate in the above-described process, p-methoxybenzyl dl-3-p-chlorophenyl-7β-(p-nitrobenzylidenamino)-3-cephem-4-carboxylate, p-methoxybenzyl dl-3-p-cyanophenyl-7β-(p-nitrobenzylideneamino)-3-cephem-4-carboxylate, p-methoxybenzyl dl-3-p-carbomethoxyphenyl-7β-(p-nitrobenzylideneamino)-3-cephem-4-carboxylate, p-methoxybenzyl dl-3-(4-pyridyl)-7β-(p-nitrobenzylideneamino)-3-cephem-4-carboxylate, p-methoxybenzyl dl-3-(2-furyl)-7β-(p-nitrobenzylideneamino)-3-cephem-4-carboxylate and p-methoxybenzyl dl-3-(5-methyl-2-furyl)-7β-(p-nitrobenzylideneamino)-3-cephem-4-carboxylate are obtained.

The p-methoxybenzyl dl-3-p-carbomethoxyphenyl-7β-(p-nitrobenzylideneamino)-3-cephem-4-carboxylate prepared in this manner has the following characteristics. NMR (δ, CDCl$_3$): 8.73 (CH=N), other peaks correct.

Step C: p-Methoxybenzyl dl-3-phenyl-7β-amino-3-cephem-4-carboxylate p-Methoxybenzyl dl-3-phenyl-7β-(p-nitrobenzylideneamino)-3-cephem-4-carboxylate (180 mg.) is treated with 163 mg. of 2,4-dinitrophenylhydrazine tosylate in 6 ml. of ethanol. The mixture is stirred 30 minutes, filtered, evaporated, treated with pH 8.0 aqueous buffer and extracted 3 times with ether. The combined ether extracts are dried with MgSO$_4$, filtered and evaporated, leaving 140 mg. of p-methoxybenzyl dl-3-phenyl-7β-amino-3-cephem-4-carboxylate. IR (μ): 3.0 (NH$_2$), 5.64 (lactam), 5.74 (ester).

When p-methoxybenzyl dl-3-p-chlorophenyl-7β-(p-nitrobenzylideneamino)-3-cephem-4-carboxylate, p-methoxybenzyl dl-3-p-cyanophenyl-7β-(p-nitrobenzylideneamino)-3-cephem-4-carboxylate, p-methoxybenzyl dl-3-p-carbomethoxyphenyl-7β-(p-nitrobenzylideneamino)3-cephem-4-carboxylate, p-methoxybenzyl dl-3-(4-pyridyl)-7β-(p-nitrobenzylideneamino)-3-cephem-4-carboxylate, p-methoxybenzyl dl-3-(2-furyl)-7β-(p-nitrobenzylidenemino)-3-cephem-4-carboxylate and p-methoxybenzyl dl-3-(5-methyl-2-furyl)-7β-(p-nitrobenzylideneamino)-3-cephem-4-carboxylate are used in place of p-methoxybenzyl dl-3-phenyl-7β-(p-nitrobenzylideneamino)-3-cephem-4-carboxylate in the above described process, p-methoxybenzyl dl-3-p-chlorophenyl-7β-amino-3-cephem-4-carboxylate, p-methoxybenzyl dl-3-p-cyanophenyl-7β-amino-3-cephem-4-carboxylate, p-methoxybenzyl dl-3-p-carbomethoxyphenyl-7β-amino-3-cephem-4-carboxylate, p-methoxybenzyl dl-3-(4-pyridyl)-7β-amino-3-cephem-4-carboxylate, p-methoxybenzyl dl-3-(2-furyl)-7β-amino-3-cephem-4-carboxylate and p-methoxybenzyl dl-3-(5-methyl-2-furyl)-7β-amino-3-cephem-4-carboxylate are obtained.

The p-methoxybenzyl dl-3-p-carbomethoxyphenyl-7β-amino-3-cephem-4-carboxylate obtained by this process has the following characteristics. NMR (δ, CDCl$_3$): 8.73 (CH=N), other peaks correct.

EXAMPLE 12 p-Methoxybenzyl 3-(4-pyridyl)-7β-amino decephalosporanate

Step A:

p-Methoxybenzyl 3-(4-pyridyl)-7α-amino decephalosporanate, 117 mg. is hydrogenated in 10 ml. benzene 1 hour at 40 psi with 100 mg. PtO$_2$, repeating twice more with fresh catalyst. After filtration and evaporation, p-methoxybenzyl 3-(4-pyridyl)-7α-amino decephalosporanate is obtained. IR (μ, film): 3.0, NH$_2$; 5.63, β-lactam; 5.76, ester. MS: 397, 356, 341, 218, 175, 121.

Step B: p-Methoxybenzyl 3-(4-pyridyl)-7α(p-nitrobenzylideneamino)decephalosporanate p-Methoxybenzyl 3-(4-pyridyl)-7α-amino decephalosporanate, 50 mg., is treated with 99 mg. p-nitrobenzaldehyde in 10 ml. CH$_2$Cl$_2$ containing 1 g. MgSO$_4$ for 2 hours. Filtration and evaporation afford p-methoxybenzyl 3-(4-pyridyl)-7α-(p-nitrobenzylideneamino)decephalosporanate.

Step C: p-Methoxybenzyl 3-(4-pyridyl)-7β-(p-nitrobenzylideneamino)decephalosporanate p-Methoxybenzyl 3-(4-pyridyl)-7α-(p-nitrobenzylideneamino)decephalosporanate, 120 mg., in 20 ml. THF, is added at −78° C. under N$_2$ to a solution of 130 λ 2.3M φLi in 6 ml. THF. DMF, 15 ml., is added, followed by 0.3 ml. AcOH in 2 ml. THF. The reaction mixture is warmed to 25° C., diluted with benzene and washed 6 times with water. Wash No. 5, has pH 8.0 phosphate buffer. After drying with MgSO$_4$, filtration and evaporation, p-methoxybenzyl 3-(4-pyridyl)-7β-(p-nitrobenzylideneamino)decephalosporanate is obtained in a 1:1 mixture with p-methoxybenzyl 3-(4-pyridyl)-7α-(p-nitrobenzylideneamino)decephalosporanate.

Step D: p-Methoxybenzyl 3-(4-pyridyl)-7β-aminodecephalosporanate p-Methoxybenzyl 3-(4-pyridyl)-7β-(p-nitrobenzylideneamino)decephalosporanate, 120 mg., in ½ml. CH$_2$Cl$_2$, is added to 88 mg. 2,4-dinitrophenylhydrazine tosylate in 5 ml. EtOH and stirred 30 minutes, filtered and evaporated. The residue is treated with pH 8.0 aqueous phosphate, extracted 3 × with ether, dried with MgSO$_4$, filtered and evaporated, affording p-methoxybenzyl 3-(4-pyridyl)-7β-aminodecephalosporanate.

EXAMPLE 13 p-Methoxybenzyl 3-(4-thiazolyl)-7β-aminodecephalosporanate

Step A: p-Methoxybenzyl 3-(4-thiazolyl)-7α-(p-nitrobenzylideneamino)decephalosporanate p-Methoxybenzyl 3-(4-thiazolyl)-7α-aminodecephalosporanate, 380 mg. is treated with 750 mg. p-nitrobenzaldehyde in 60 ml. CH$_2$Cl$_2$ containing 2 g. MgSO$_4$ for 2 hours. Filtration and evaporation afford 420 mg. crude crystalline material which gives 220 mg. pure p-methoxybenzyl 3-(4-thiazolyl)-7α-(p-nitrobenzylideneamino)decephalosporanate after recrystallization from benzene-cyclohexane. IR (μ, Nujol): 5.58, β-lactam; 5.76, ester. NMR (δ, CDCl$_3$): 5.03d, 5.06d, J=2, H-6 and H-7; 5.26s, OCH$_2$; 8.58 O$_2$NC$_6$H$_4$CH=N; other peaks correct.

Step B: p-Methoxybenzyl 3-(4-thiazolyl)-7β-(p-nitrobenzylideneamino)decephalosporanate p-Methoxybenzyl 3-(4-thiazolyl)-7α-(p-nitrobenzylideneamino)decephalosporanate, 40 mg. in 7 ml. THF, is added at −78° C. under N$_2$ to a solution of 10 λ Et$_3$N and 33 λ 2.3M φLi in 2 ml. THF. DMF, 5 ml., is added, followed by 0.1 ml. AcOH in 0.5 ml. THF. The reaction mixture is warmed to 25° C., diluted with benzene and washed 6 × with water; wash No. 2 has pH 3.0 phosphate and wash No. 5, pH 8.0. After drying with MgSO$_4$ and evaporatiob, a 1:1 mixture of p-methoxybenzyl 3-(4-thiazolyl)-7β-(p-nitrobenzylideneamino)decephalosporanate and p-methoxybenzyl 3-(4-thiazolyl)-7α-(p-nitrobenzylideneamino)decephalosporanate is obtained. IR is like p-methoxybenzyl 3-(4-thiazolyl)-7α-(p-nitrobenzylideneamino)decephalosporanate. NMR (δ, CDCl$_3$) shows p-methoxybenzyl 3-(4-thiazolyl)-7α-(p-nitrobenzylideneamino)decephalosporanate and p-methoxybenzyl 3-(4-thiazolyl)-7β-(p-nitrobenzylideneamino)decephalosporanate: 5.15d, J=5, 6-H; 5.55q, J=5, 1.5, 7-H; 8.72, O$_2$NC$_6$H$_4$CH=N; other peaks correct.

Step C: p-Methoxybenzyl 3-(4-thiazolyl)-7β-aminodecephalosporanate 180 mg. p-Methoxybenzyl 3-(4-thiazolyl)-7β-(p-nitrobenzylideneamino)decephalosporanate in ½ ml. CH$_2$Cl$_2$ is added to 131 mg. 2,4-dinitrophenylhydrazine tosylate in 5 ml. EtOH and stirred 10 minutes, filtered and evaporated. The residue is treated with pH 8.0 aqueous phosphate, extracted 3 × with ether, dried with MgSO$_4$, filtered and evaporated, leaving p-methoxybenzyl 3-(4-thiazolyl)-7β-aminodecephalosporanate. IR (μ, film): 3.0, NH$_2$; 5.65, β-lactam; 5.80, ester. NMR (δ, CDCl$_3$): 4.73d, 4.98d, J=5, H-6 and H-7; other peaks correct.

EXAMPLE 14 p-Methoxybenzyl dl-3-(1-acetoxyethyl)-7β-amino-3-cephem-4-carboxylate

Step A: p-Methoxybenzyl dl-3-(1-acetoxyethyl)-7α-(p-nitrobenzylideneamino)-3-cephem-4-carboxylate p-Methoxybenzyl dl-3-(1-acetoxyethyl)-7α-amino-3-cephem-4-carboxylate (101 mg.) is treated with 36 mg. p-nitrobenzaldehyde and 0.7 g. of magnesium sulfate in 5 ml. of methylene chloride with stirring for 13 hours. The solution is filtered and evaporated to afford p-methoxybenzyl dl-3-(1-acetoxyethyl)-7α-(p-nitrobenzylideneamino)-3-cephem-4-carboxylate in 80% yield. Properties: IR (CHCl$_3$) 3.45, 5.62, 5.78, 5.81, 6.1, 6.23, 6.68, 6.89, 7.3, 7.42, 8.2, 8.5, 8.9, 11.0, 11.65, 12.05μ. NMR (CDCl$_3$) τ8.56 (d, 3, J=8 Hz, CHCH$_3$), 8.0 (s, 3 CH$_3$CO), 6.5 (s, 2, ScH$_2$), 6.18 (s, 3, OCH$_3$), 5.15 (d, 1, J=1, 2 Hz, H-6 or H-7), 5.07, (d, 1, J=1.2 Hz, H-7 or H-6), 4.75 (s, 2, ArCH$_2$), 4.0 (q, 1, J=8 Hz, CHCH$_3$), 2.82 (ABq, 4, ArH), 2.0 (ABq, 4, ArH), 1.42 (s, 1, CH=N).

Step B: p-Methoxybenzyl dl-3-(1-acetoxyethyl)-7β-(p-nitrobenzylideneamino)-3-cephem-4-carboxylate p-Methoxybenzyl dl-3-(1-acetoxyethyl)-7α-(p-nitrobenzylideneamino)-3-cephem-4-carboxylate (130 mg.) is dissolved in 4 ml. tetrahydrofuran. At −78° C. under nitrogen, 0.163 ml. 2.3 M phenyl lithium is added, forming the 7-lithium derivative of p-methoxybenzyl dl-3-(1-acetoxyethyl)-7α-(p-nitrobenzylideneamino)-3-cephem-4-carboxylate. Dimethylformamide (5 ml.) is added, and then a mixture of 3 ml. tetrahydrofuran, 0.063 ml. of acetic acid and 0.020 ml. of water. The reaction mixture is warmed to room temperature, diluted with 50 ml. benzene and washed 6 times with water. Wash No. 2 contains pH 2.0 phosphate buffer, and wash No. 5, pH phosphate buffer. After drying with magnesium sulfate, filtration and evaporation of the solvent, a mixture of p-methoxybenzyl dl-3-(1-acetoxyethyl)-7β-(p-nitrobenzylideneamino)-3-cephem-4-carboxylate and p-methoxybenzyl dl-3-(1-acetoxyethyl)-7α-(p-nitrobenzylideneamino)-3-cephem-4-carboxylate in 85% yield is obtained. The normal isomer shows new bands in the NMR spectrum at τ4.9 and 4.5 (H-6 and H-7) and τ1.2 (CH=N).

Step C: p-Methoxybenzyl dl-3-(1-acetoxyethyl)-7β-amino-3-cephem-4-carboxylate

A mixture of p-methoxybenzyl dl-3-(1-acetoxyethyl)-7β-(p-nitrobenzylideneamino)-3-cephem-4-carboxylate and its 7α-epimer (180 mg.) is treated with 163 mg. of 2,4-dinitrophenylhydrazine tosylate in 6 ml. of ethanol. The mixture is stirred 30 minutes, filtered, evaporated, treated with pH 8.9 aqueous buffer and extracted 3 times with ether. The combined ether extracts are dried with MgSO$_4$, filtered and evaporated, leaving a mixture of p-methoxybenzyl dl-3-(1-acetoxyethyl)-7β-amino-3-cephem-4-carboxylate and its 7α-epimer in 97% yield. Properties: NMR (CDCl$_3$) τ 8.72 (d, 3, J=8 Hz, CHCH$_3$), 8.0 (s, 3, CH$_3$CO), 7.5 (brs, 2, NH$_2$), 6.6 (s, 2, SCH$_2$), 6.3 (s, 3, OCH$_3$), 5.4 (d, 1, J=4.5 Hz, H-6 or H-7), 5.17 (d, 1, J=4.5 Hz, H-7 or H-6), 4.8 (s, 2, CH$_2$Ar), 4.0 (q, 1, J=8 Hz, CHCH$_3$), 2.95 (ABq, 4, ArH).

Purification by silica gel column chromatography or silica gel preparative thin layer chromatography affords pure p-methoxybenzyl d, 1-3-(1-acetoxyethyl)-7β-amino-3-cephem-4-carboxylate.

The p-methoxybenzyl dl-3-p-carbomethoxyphenyl-7α-amino-3-cephem-4-carboxylate obtained in this way exhibits the following characteristics. IR (μ): 3.0 (NH), 5.62 (lactam), 5.79 (ester. NMR (δ, CDCl$_3$): 4.24d, 4.85d, J=2 Hz (H-6, H-7), 2.3 broad (NH$_2$), other peaks correct. MS: 454, 398, 332, 232, 121.

EXAMPLE 15

Dimethyl d,1-3-acetoxymethyl-7β-amino-3-cephem-4-phoshonate

Step A: Dimethyl d,1-3-acetoxymethyl-7α-(p-nitrobenzylideneamino)-3-cephem-4-phosphonate A mixture of dimethyl d,1-3-acetoxymethyl-7α-amino-3-cephem-4-phosphonate (403 mg., 1.2 mmol.) p-nitrobenzaldehyde (181 mg., 1.2 mmol.), magnesium sulfate (3.0g.) and methylene chloride (30 ml.) is stirred for two hours at room temperature. The mixture is filtered and the filtrate is evaporated under reduced pressure to yield dimethyl d,1-3-acetoxymethyl-7α-(p-nitrobenzylideneamino)-3-cephem-4-carboxylate.

Step B: Dimethyl d,1-3-acetoxymethyl-7β-(p-nitrobenzylideneamino)-3-cephem-4-phosphonate Anhydrous tetrahydrofuran (20 ml.) and dimethyl d,1-3-acetoxymethyl-7α-(p-nitrobenzylideneamino)-3-cephem-4-phosphonate (562 mg., 1.2 mmol.) are stirred at −78° C. under an atmosphere of nitrogen. Phenyl lithium (0.52 ml. of a 2.3 M solution in 7:3 benzene-ether) is added, forming the deep blue anion. Dimethylformamide (25 ml.) is added dropwise over a period of 15 minutes and after one more minute at −78° C. a solution of water of (216 mg.) and acetic acid (180 mg.)

in tetrahydrofuran (20 ml.) is added. The reaction mixture is allowed to warm to room temperature, then diluted with benzene (400 ml.) and washed with water (6 × 200 ml.). The second wash is acidified with pH 2.0 phosphate buffer, and the fifth basified with pH 9.0 buffer. The benzene solution is dried over magnesium sulfate, filtered and evaporated in vacuo to give a mixture of dimethyl d,1-3-acetoxymethyl-7β-(p-nitrobenzylideneamino)-3-cephem-4-phosphonate and dimethyl d,1-3-acetoxymethyl-7α-(p-nitrobenzylideneamino)-3-cephem-4-phosphonate.

Step C: Dimethyl d,1-3-acetoxymethyl-7β-amino-3-cephem-4-phosphonate

The mixture of dimethyl d,1-3-acetoxymethyl-7-(p-nitrobenzylideneamino)-3-cephem-4-carboxylates (548 mg., 1.17 mmol.) obtained in the previous example is dissolved in chloroform (4 ml.) and added to a solution of 2,4-dinitrophenylhydrazine p-toluenesulfonic acid in ethanol (prepared from 232 mg. of 2,4-dinitrophenylhydrazine and 223 mg. of toluenesulfonic acid monohydrate stirred in 35 ml. of ethanol for 45 minutes). The reaction mixture is stirred for 30 minutes, filtered and the filtrate is evaporated in vacuo. The residue is treated with aqueous pH 9.0 phosphate buffer and extracted three times with ether. The combined extracts are dried over magnesium sulfate, filtered and evaporated in vacuo to provide a mixture of dimethyl d,1-3-acetoxymethyl-7β-amino-3-cephem-4-phosphonate and dimethyl d,1-3-acetoxymethyl-7α-amino-3-cephem-4-phosphonate.

EXAMPLE 16

Di-t-butyl-d,1-7β-amino-3-acetoxymethyl-3-cephem-4-phosphonate

Step A: Di-t-butyl d,1-7α-(p-nitrobenzylideneamino)-3-acetoxymethyl-3-cephem-4-phosphonate A mixture of di-t-butyl d,1-7α-amino-3-acetoxymethyl-3-cephem-4-phosphonate (0.42 g.), p-nitrobenzaldehyde (0.14 g.), magnesium sulfate (2.0 g.), and methylene chloride (20 ml.) is stirred overnight at room temperature in a capped flask. The mixture is filtered and the filtrate is evaporated in vacuo to hield di-t-butyl d,1-7α-(p-nitrobenzylideneamino)-3-acetoxymethyl-3-cephem-4-phosphonate.

Step B: Di-tu-butyl d,1-7β-(p-nitrobenzylideneamino)-3-acetoxymethyl-3-cephem-4-phosphonate A solution of di-t-butyl d,1-7α-(p-nitrobenzylideneamino)-3-acetoxymethyl-3-cephem-4-phosphonate (0.53 g.) in anhydrous tetrahydrofuran (15 ml.) is cooled to −78° C. under nitrogen. Phenyl lithium (0.41 ml. of a 2.3 M solution) is added rapidly with stirring. Anhydrous dimethylformamide (20 ml.) is then added dropwise over a period of 5 minutes. After having been stirred an additional one minute at −78° C., the reaction mixture is quenched with a solution of water (0.17 ml.) and acetic acid (0.13 ml.) in tetrahydrofuran (5 ml.). The mixture is allowed to warm to room temperature. Benzene (200 ml.) is added to the mixture and the resulting solution is washed with water (6 × 100 ml.). The second wash is acidified with pH 3.0 phosphate buffer. The benzene solution is dried over magnesium sulfate, filtered and evaporated in vacuo to afford a mixture of di-t-butyl-7β-(p-nitrobenzylideneamino)-3-acetoxymethyl-3-cephem-4-phosphonate and the corresponding 7α-isomer.

Step C: Di-t-butyl d,1-7β-(and 2)-amino-3-acetoxymethyl-3-cephem-4-phosphonate 2,4-Dinitrophenylhydrazine (182 mg.) is added to a stirring solution of p-toluenesulfonic acid monohydrate (175 mg.) in ethanol (25 ml.). The mixture is stirred at room temperature for 30 minutes, and then treated with a solution of di-t-butyl d,1-7βand 7α-(p-nitrobenzylideneamino)-3-acetoxymethyl-3-cephem-4-phosphonate (0.53 g.) in chloroform (5 ml.). After stirring for 30 minutes at room temperature, the mixture is filtered and the filtrate is evaporated in vacuo. The residue is partioned between ether (50 ml.) and water (10 ml.) containing 1 M dipotassium hydrogen phosphonate (2 ml.). The ethereal phase is dried with magnesium sulfate, filtered and evaporated in vacuo to afford a mixture of di-t-butyl-d,1-7β-amino-3-acetoxymethyl-3-cephem-4-phosphonate and the 7α-amino isomer.

EXAMPLE 17

Dimethyl d,1-7β-amino-3-methyl-3-cephem-4-phosphonate

Step A: Dimethyl d,1-7α-(p-nitrobenzylideneamino)-3-methyl-3-cephem-4-phosphonate A mixture of dimethyl d,1-7α-amino-3-methyl-3-cephem-4-phosphonate (0.31 g.), p-nitrobenzaldehyde (0.13 g.) and magnesium sulfate (1.6 g.) in methylene chloride (20 ml.) is stirred at room temperature and under nitrogen for 18 hours. The mixture is filtered and the filtrate evaporated in vacuo. Trituration of the residue with diethyl ether yields crystalline dimethyl d,1-7α-(p-nitrobenzylideneamino)-3-methyl-3-cephem-4-phosphonate (0.17 g.): IR ($CH_2Cl_2$) 5.61, 6.10, 6.24 and 9.7μ; NMR ($CDCl_3$) δ 2.36 (d, 3, J=3$H_z$, $CH_3$), 3.35 (s, 2, $SCH_2$), 3.84 and 3.90 (two doublets, 6. J=12$H_z$, $OCH_3$), 4.87 (d, 1, J=1.5 $H_z$, H-6 or H-7), 4.94 (d, 1, J=1.5$H_z$, H-7 or H-6), 7.99 and 8.32 (two doublets, 4, J=9$H_z$, ArH), and 8.61 (s, 1, CH=N).

Step B: Dimethyl d,1-7β-(p-nitrobenzylideneamino)-3-methyl-3-cephem-4-phosphonate A solution of dimethyl d,1-7α-(p-nitrobenzylideneamino)-3-methyl-3-cephem-4-phosphonate (0.19 g.) in anhydrous tetrahydrofuran (6 ml.) is cooled to −78° C. under nitrogen. Phenyl lithium (0.2 ml. of a 2.3 M solution) is added with stirring. Anhydrous dimethylformamide (8.9 ml.) is then added dropwise over 4 minutes. After stirring an additional 1.5 minutes at −78° C., the reaction mixture is quenched by addition of a solution of water (83 ml.) and acetic acid (66 ml.) in tetrahydrofuran (6.5 ml.). The mixture is allowed to warm to room temperature Benzene (100 ml.) is added and the solution is washed with water (6 × 40 ml.). The second wash is acidified with pH 3.0 phosphate buffer (0.5 ml. of a 1 M solution) and the fifth is basified with pH 9.0 phosphate buffer (0.5 ml. of a 1 M solution). The benzene solution is dried with magnesium sulfate, filtered and evaporated in vacuo to yield a mixture of dimethyl d,1-7α-(p-nitrobenzylideneamino)-3-methyl-3-cephem-4-phosphonate and dimethyl d,1-7β-(p-nitrobenzylideneamino)-3-methyl-3-cephem-4-phosphonate.

Step C: Dimethyl d,1-7β(and 7α)-amino-3-methyl-3-cephem-4-phosphonate 2,4-Dinitrophenylhydrazine (91 mg.) is added to a solution of p-toluenesulfonic acid monohydrate (87 mg.) in ethanol (10 ml.). The resulting mixture is stirred at room temperature for 45 minutes, then treated with a solution of the Schiff base mixture obtained by the previous example in chloroform (2 ml.). The mixture is stirred at room temperature for 30 minutes, filtered and the filtrate is evaporated in vacuo. the residue is taken up in chloroform and filtered. The filtrate is washed with pH 9.0 phosphate buffer and saturated sodium chloride, dried over magnesium sulfate, filtered and evaporated in vacuo. The residue (58 mg.) is a mixture of dimethyl d,1-7α-amino-3-methyl-3-cephem-4-phosphonate and dimethyl d,1-7β-amino-3-methyl-3-cephem-4-phosphonate.

EXAMPLE 18 p-Nitrophenyl d,1-3-acetoxymethyl-7β-amino-3-cephem-4-sulfonate

Step A: p-Nitrophenyl d,1-3-acetoxymethyl-7α-(p-nitrobenzylideneamino)-3-cephem-4-sulfonate A mixture of p-nitrophenyl d,1-3-acetoxymethyl-7α-amino-3-cephem-4-sulfonate (644 mg.), p-nitrobenzaldehyde (226 mg.) anhydrous magnesium sulfate (4.0 g.) and methylene chloride (30 ml.) is stirred for two hours at room temperature. The mixture is filtered and the filtrate is evaporated under reduced pressure to yield p-nitrophenyl d,1-3-acetoxymethyl-7α-(p-nitrobenzylideneamino)-3-cephem-4-sulfonate.

Step B: p-Nitrobenzyl d,1-3-acetoxymethyl-7β-(p-nitrobenzylideneamino)-3-cephem-4-sulfonate A solution of p-nitrophenyl d,1-3-acetoxymethyl-7α-(p-nitrobenzylideneamino)-3-cephem-4-sulfonate (845 mg.) in 20 ml. under an atmosphere of nitrogen. Phenyl lithium (0.65 ml.) of a 2.3 M solution in 7:3 benzene-ether) is added dropwise over a period of 15 minutes, and after an additional minute at −78° C., a solution of water (270 mg.) and acetic acid (255 mg.) in tetrahydrofuran (25 ml.) is added. The reaction mixture is allowed to warm to room temperature, then diluted with benzene (500 ml.) and washed with six 250 ml. portions of water. The second wash is acidified with pH 2.0 phosphate buffer and the fifth basified with pH 9.0 buffer. The benzene solution is dried over magnesium sulfate, filtered and evaporated in vacuo to give a mixture of p-nitrophenyl d,1-3-acetoxymethyl-7β-(p-nitrobenzylideneamino)-3-cephem-4-sulfonate and p-nitrophenyl d,1-3-acetoxymethyl-7α-(p-nitrobenzylideneamino)-3-cephem-4-sulfonate.

Step C: p-Nitrophenyl d,1-3-acetoxymethyl-7β-amino-3-cephem-4-sulfonate

The mixture of p-nitrophenyl d,1-3-acetoxymethyl-7-(p-nitrobenzylideneamino)-3-cephem-4-sulfonate obtained in the previous example is suspended in 40 ml. of ether and p-toluenesulfonic acid hydrate (285 mg.) is added. The mixture is stirred at room temperature for 3 hours, then filtered. The filter cake is washed with ether, then resuspended in 50 ml. of chloroform and treated with N pH 9.0 phosphate buffer (50 ml.). The chloroform solution is separated, dried over anhydrous magnesium sulfate and evaporated in vacuo to provide a mixture of p-nitrophenyl d,1-3-acetoxymethyl-7β-amino-3-cephem-4-sulfonate and p-nitrophenyl d,1-3-acetoxymethyl-7α-amino-3-cephem-4-sulfonate.

EXAMPLE 19

Benzyl 6β-amino-1-oxadethiapenicillinate

Step A: Benzyl 6α-benzaldimino-1-oxadethiapencillinate

Benzyl 6α-amino-1-oxadethiapenicillinate (0.29 g.) is treated with benzaldehyde (0.106 g.). The mixture is dissolved in benzene (20 ml.), dried over magnesium sulfate, filtered and evaporated to afford benzyl 6α-benzaldimino-1-oxadethiapenicillinate.

Step B: Benzyl 6β-benzaldimino-1-oxadethiapenicillinate (0.378 g.) is dissolved in anhydrous tetrahydrofuran (16 ml.) and cooled to −78° C. (under N$_2$). Phenyl lithium (1 ml.1M) in benzene/ether is added dropwise over 2 minutes, dimethylformamide (20 ml.) is then added over 2 minutes followed by a mixture of water (0.03 ml.) and acetic acid (0.08 g.) in tetrahydrofuran (20 ml.). The reaction mixture is warmed to room temperature and diluted with benzene and washed with a pH 8.0 phosphate buffer, then dried and evaporated. The residue is a mixture of starting material and benzyl 6β-benzaldimino-1-oxadethiapenicillinate.

Step C: Benzyl 6β-amino-1-oxadethiapenicillinate 2,4-Dintrophenylhydrazine (0.198 g.) is dissolved in ethanol (10 ml.) and p-toluenesulfonic acid monohydrate (0.159 g.) is added and the mixture is allowed to stir at room temperature for ½ hour. To this is added a solution of benzyl 5-benzaldimino-1-oxadethiapenicillinate (0.378 g. of the mixture of C$_6$ epimers) in ethanol (10 ml.). The reaction mixture is stirred for ½ hour at room temperature, filtered and the filtrate evaporated. The residue is taken up in methylene chloride and washed with a pH 8.0 phosphate buffer and dried and evaporated to afford predominantly 6β-amino-1-oxadethiapenicillinate.

All of the above examples result in the preparation of 7β-amino-(or 6β-amino) compounds. As indicated, these are acylated to prepare active antibacterial agents. This acylation process if indicated in the following examples.

EXAMPLE 20

Step A: p-Methoxybenzyl dl-3-phenyl-7β(2-thienylacetamide)-3-cephem-4-carboxylate To a solution of 140 mg. p-methoxybenzyl dl-3-phenyl-7β-amino-3-cephem-4-carboxylate from Example 11 in 10 ml. of methylene chloride is added successively 0.14 ml. pyridine and a solution of 57 mg. 2-thienylacetyl chloride in 4 ml. of methylene chloride. After 5 minutes stirring at room temperature, the solvent is evaporated and replaced with benzene. The solution is washed with pH 2.0 phosphate buffer, water, and pH 8.0 phosphate buffer. After drying with magnesium sulfate, filtration and evaporation of the solvent, p-methoxybenzyl dl-3-phenyl-7β(2-thienylacetamido)-3-cephem-4-carboxylate is obtained. It is purified by chromatography on 6 g. silica gel, eluting with 10:1 chloroform-ethyl acetate, which affords 27 mg. p-methoxybenzyl dl-3-phenyl-7β(2-thienylacetamido)-3-cephem-4-carboxylate. IR ($\mu$): 3.06 (NH), 5.63 (lactam), 5.77 (ester), 5.97 (amide). NMR ($\delta$, CDCl$_3$): 3.14, 3.59, 3.82, 4.17 (SCH$_2$); 3.78 (CH$_2$CO); 4.9m (OCH$_2$, 6-H); 5.76, 5.83, 5.97 (7α-H). MS: 520, 355, 339, 181.

Step B: Sodium dl-3-phenyl-7β-(2-thienylacetamido)-3-cephem-4-carboxylate p-Methoxybenzyl dl-3-phenyl-7β(2-thienylacetamido)-3-cephem-4-carboxylate (24 mg.) is dissolved in 0.5 ml. anisole and treated with 2.5 ml. trifluoroacetic acid for 5 minutes at 0° C. The trifluoroacetic acid is pumped off in vacuo at 25° C. and the anisole at ca. 30° C/0.1 mm. More anisole (2 ml.) is added and pumped off. The sample is taken up in 5 ml. water containing 3 equivalents of sodium bicarbonate and washed with methylene chloride 3 times. The water layer is acidified to pH 2.0 with phosphate buffer and extracted with ethyl acetate. The ethyl acetate is then extracted with water containing 3 mg. sodium bicarbonate and the water lyophilized, affording crystalline sodium dl-3-phenyl-7β-(2-thienylacetamido)3-cephem-4-carboxylate (13 mg.) which has antibacterial activity. IR (acid form): 5.60μ (lactam). NMR (Na salt, D₂O, δ,: 3.92 (SCH₂), 4.13 (CH₂CO), 4.86 (HDO), 5.38d, 5.90d, J=4.5 Hz (H-6, H-7). High resolution MS of methyl ester (from acid form and CH₂N₂): 414.0713; calc. for $C_{20}H_{18}N_2O_4S_2$, 414.0707.

What is claimed is:

1. The process of epimerizing a compound having the formula

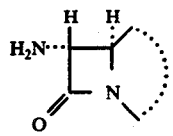

wherein the symbol indicated as a curved broken line represents the following:

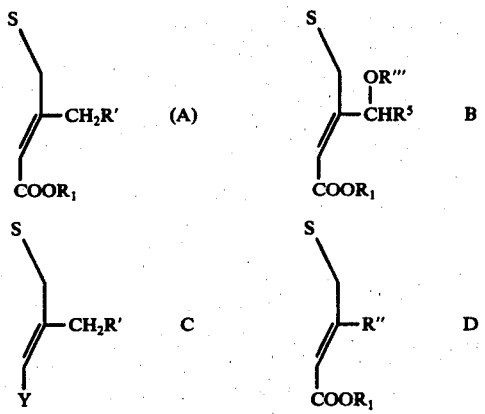

wherein $R_1$ is an easily removable ester blockingg group; R' is hydrogen, halo, loweralkanoyloxy, carbamoyloxy, furyl, thiazolyl, thiazolyl, thiadiazolyl, pyrrolyl, or tetrazolyl; each of which can be substituted with a lower alkyl substituent of 1-6 carbon atoms; R" is phenyl, furyl, thienyl, thiazolyl, thiadiazolyl, pyridyl, pyrazolyl, or tetrazolyl; R''' is loweralkanoyl; R⁵ is loweralkyl; and Y is PO(OH)₂ (OR⁴), SO₂(OH) or SO₂NH₂ in which R⁴ is loweralkyl;

a. which comprises reacting the compound above with an aromatic or aliphatic aldehyde or ketone to yield an intermediate of the formula

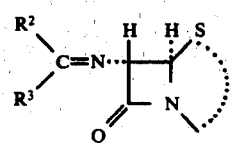

wherein the broken curved line is as defined, and R² is lower-alkyl or phenyl and R³ is hydrogen, loweralkyl or phenyl;

b. and treating the latter intermediate with a base sufficiently strong to convert the aldimino compound to its anionic form said treatment conducted in the presence of an aprotic solvent and the optional presence of a dipolar aprotic co-solvent, followed by addition of a molecular excess of acid, a carboxylic acid having from 1-5 carbon atoms;

c. and reacting the compound thereby produced with acid in the optional presence of an amine, and recovering the product,

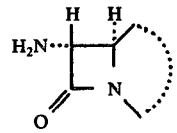

wherein the curved broken line is as defined above.

2. The process of Step (A) of claim 1 wherein a solvent is employed.

3. The process of claim 2 wherein the solvent is methylene chloride.

4. The process of claim 2 wherein the reaction is conducted at ambient temperature.

5. The process of Step (A) of claim 1 wherein the reactants are employed in approximately equimolar amounts.

6. The process of Step (B) of claim 1 wherein the aprotic solvent is tetrahydrofuran.

7. The process of Step (B) of claim 1 wherein the dipolar aprotic solvent is dimethylformamide, dimethylsulfoxide, hexamethylphosphoramide N-methyl pyrrolidone, or dimethylacetamide.

8. The process of Step (B) of claim 1 wherein the strong base is an organosodium, organopotassium or organolithium compound.

9. The process of claim 8 wherein the strong base is phenyl lithium, t-butyl lithium or n-butyl lithium.

10. The process of claim 1 in which the acid is acetic acid.

11. The process of Step (C) of claim 1 wherein the amine is aniline, phenylhydrazine, or 2,4-dinitrophenylhydrazine.

12. The process of Step (C) of claim 1 wherein the acid is hydrochloric acid or p-toluenesulfonic acid.

13. The process of Step (C) of claim 1 wherein aniline hydrochloride is used as the amine in the presence of acid.

14. The process of step (C) of claim 1 wherein the amine if is 2,4-dinitrophenylhydrazine and the acid is p-toluenesulfonic acid.

15. The process of Step (C) of claim 1 wherein an alcoholic solvent is used.

16. The process of Step (B) of claim 1 wherein the solvent is a lower alcohol having 1-5 carbon atoms.

17. The process of claim 1 wherein $R_1$ is alkyl, of from 1-20 carbon atoms, phthalimidomethyl, succinimidomethyl, phenacyl, p-bromophenacyl, 2,2,2-trichloroethyl, 2-methylthioethyl, 2-(p-methylphenyl)ethyl, methoxymethyl, p-methoxyphenoxymethyl, benzyloxymethyl, benzyl, p-nitrobenzyl, p-methoxybenzyl, 3,5-dinitrobenzyl, 2,4,6-trimethylbenzyl or 3,5-dichloro-4-hydroxy-benzyl, benzhydryl, p-methoxybenzhydryl, or trimethylsilyl.

18. The process of claim 17 wherein $R_1$ is methyl, tertiary butyl, phenacyl, p-bromophenacyl, 2,2,2-trichloroethyl, p-methoxybenzyl, benzyl, benzhydryl, methoxymethyl, and p-methoxyphenoxymethyl.

19. The process of claim 1 wherein the R' is 5-methyl-1,3,4-thiadiazolyl-2-yl or 1-methyl-tetrazol-5yl.

20. The process of claim 1 wherein the R" is substituted with lower alkyl of 1-6 carbon atoms, or lower alkoxy of 1-6 carbon atoms.

21. The process of claim 1 wherein R''' is loweralkanoyl having 2-6 carbon atoms.

22. The process of claim 1 wherein R⁵ is $C_1$-$C_3$ straight or branched chain alkyl.

* * * * *